(12) United States Patent
Dennis et al.

(10) Patent No.: US 12,048,810 B2
(45) Date of Patent: Jul. 30, 2024

(54) RESPIRATORY THERAPY APPARATUS AND METHOD

(71) Applicant: ResMed Pty Ltd, Bella Vista (AU)

(72) Inventors: Clancy John Dennis, Sydney (AU); Liam Holley, Sydney (AU); Gordon Joseph Malouf, Sydney (AU); Dion Charles Chewe Martin, Sydney (AU); Peter Wlodarczyk, Sydney (AU)

(73) Assignee: ResMed Pty Ltd (AU)

( * ) Notice: Subject to any disclaimer, the term of this patent is extended or adjusted under 35 U.S.C. 154(b) by 627 days.

(21) Appl. No.: 15/554,302

(22) PCT Filed: Mar. 14, 2016

(86) PCT No.: PCT/AU2016/050177
§ 371 (c)(1),
(2) Date: Aug. 29, 2017

(87) PCT Pub. No.: WO2016/145483
PCT Pub. Date: Sep. 22, 2016

(65) Prior Publication Data
US 2018/0169361 A1 Jun. 21, 2018

(30) Foreign Application Priority Data
Mar. 13, 2015 (AU) .............................. 2015900907

(51) Int. Cl.
*A61M 16/00* (2006.01)
*A61B 5/00* (2006.01)
(Continued)

(52) U.S. Cl.
CPC ......... *A61M 16/024* (2017.08); *A61B 5/0826* (2013.01); *A61B 5/4833* (2013.01);
(Continued)

(58) Field of Classification Search
CPC ............ A61M 16/024; A61M 16/0006; A61M 16/0003; A61M 16/0069; A61M 16/0633;
(Continued)

(56) References Cited

U.S. PATENT DOCUMENTS 5,335,654 A * 8/1994 Rapoport .............. A61M 16/00
128/204.23
5,551,419 A * 9/1996 Froehlich .......... A61M 16/0069
128/204.26

(Continued)

FOREIGN PATENT DOCUMENTS

CN 101365509 A 2/2009
EP 0527639 A2 2/1993
(Continued)

OTHER PUBLICATIONS

Sivieri, E.M. et al., Effect of HFNC Flow Rate, Cannula Size, and Nares Diameter on Generated Airway Pressures: An In Vitro Study, Pediatric Pulmonology 48(5) pp. 506-514 (May 2013) p. 512, col. 2 II. 18-20.

(Continued)

*Primary Examiner* — Kendra D Carter
*Assistant Examiner* — Arielle Wolff
(74) *Attorney, Agent, or Firm* — Botos Churchill IP Law LLP

(57) ABSTRACT

A method, such as in a controller associated with a respiratory therapy device, determines whether high flow therapy is being used by a patient. The method may include determining whether a property of a flow of air being delivered by a respiratory therapy device along an air circuit to an unsealed patient interface contains a significant oscillation within a breathing rate frequency band. The method may (Continued)

also include generating, dependent on the determination, an indication of whether high flow therapy is being used by the patient.

32 Claims, 13 Drawing Sheets

(51) Int. Cl.
  A61B 5/08    (2006.01)
  A61M 16/06   (2006.01)
  A61M 16/10   (2006.01)
  A61M 16/16   (2006.01)
  A61M 16/20   (2006.01)
(52) U.S. Cl.
  CPC .... *A61M 16/0003* (2014.02); *A61M 16/0006* (2014.02); *A61M 16/0051* (2013.01); *A61M 16/0069* (2014.02); *A61M 16/0633* (2014.02); *A61M 16/0666* (2013.01); *A61M 16/107* (2014.02); *A61M 16/16* (2013.01); *A61M 16/208* (2013.01); *A61M 2016/0027* (2013.01); *A61M 2016/003* (2013.01); *A61M 2016/0033* (2013.01); *A61M 16/0066* (2013.01); *A61M 16/06* (2013.01); *A61M 2205/15* (2013.01); *A61M 2205/18* (2013.01); *A61M 2205/3317* (2013.01); *A61M 2205/3334* (2013.01); *A61M 2205/3365* (2013.01); *A61M 2205/3368* (2013.01); *A61M 2205/3584* (2013.01); *A61M 2205/502* (2013.01); *A61M 2205/52* (2013.01); *A61M 2205/581* (2013.01); *A61M 2205/8206* (2013.01); *A61M 2230/42* (2013.01); *A61M 2230/46* (2013.01)
(58) Field of Classification Search
  CPC ............ A61M 16/107; A61M 16/0666; A61M 16/208; A61M 16/0051; A61M 16/16; A61M 2205/18; A61M 2016/003; A61M 2205/8206; A61M 16/0066; A61M 2205/3334; A61M 2230/42; A61M 16/06; A61M 2230/46; A61M 2205/3368; A61M 2205/15; A61M 2016/0033; A61M 2205/3317; A61M 2205/3365; A61M 2205/3584; A61M 2205/52; A61M 2205/581; A61M 2016/0027; A61M 2205/502; A61M 2016/0015; A61M 2205/3331; A61M 2205/3327; A61B 5/4833; A61B 5/0826; A61B 5/08; A61B 5/0816; A61B 5/082; A61B 5/087; A61B 5/097; A61B 5/103; A61B 5/4809; A61B 5/4818; A61B 5/4836; A61B 5/7221; A61B 5/7246; A61B 5/7264; A61B 5/7275; A61B 5/746; G08B 21/02; G16H 50/30
  See application file for complete search history.

(56) References Cited

U.S. PATENT DOCUMENTS

| | | | |
|---|---|---|---|
| 6,240,921 B1* | 6/2001 | Brydon | A61M 16/024 128/205.25 |
| 8,631,799 B2 | 1/2014 | Davenport et al. | |
| 2002/0029004 A1* | 3/2002 | Starr | A61M 16/0858 600/538 |
| 2004/0123866 A1* | 7/2004 | Berthon-Jones | A61M 16/06 128/204.23 |
| 2005/0188991 A1* | 9/2005 | Sun | A61B 5/411 128/204.23 |
| 2009/0266360 A1* | 10/2009 | Acker | A61M 16/0006 128/204.21 |
| 2010/0024816 A1* | 2/2010 | Weinstein | A61M 11/042 128/203.27 |
| 2011/0114098 A1 | 5/2011 | McAuley et al. | |
| 2011/0313689 A1* | 12/2011 | Holley | A61M 16/024 702/56 |
| 2012/0291783 A1* | 11/2012 | Peiris | A61M 16/109 128/204.21 |
| 2015/0283342 A1* | 10/2015 | Mielcarz | G09B 23/288 128/205.13 |
| 2016/0015918 A1* | 1/2016 | Kuriger | A61M 16/205 128/204.23 |
| 2016/0121063 A1* | 5/2016 | Tatkov | A61M 16/026 128/204.23 |
| 2016/0193438 A1* | 7/2016 | White | A61M 16/0069 128/204.23 |

FOREIGN PATENT DOCUMENTS

| | | | | |
|---|---|---|---|---|
| WO | 2005067520 A2 | 7/2005 | | |
| WO | 2008060295 A2 | 5/2008 | | |
| WO | 2011/068418 A1 | 6/2011 | | |
| WO | WO-2011068418 A1 * | 6/2011 | ........ | A61M 16/0051 |
| WO | WO-2013177621 A1 * | 12/2013 | .......... | A61B 5/7275 |
| WO | 2014/095736 A1 | 6/2014 | | |
| WO | 2014095736 A1 | 6/2014 | | |
| WO | 2015/033288 A1 | 3/2015 | | |

OTHER PUBLICATIONS

International Search Report for PCT/AU2016/050177 filed Mar. 14, 2016.

Written Opinion mailed Jun. 7, 2016 for PCT/AU2016/050177 filed Mar. 14, 2016.

Written Opinion mailed Feb. 24, 2017 for PCT/AU2016/050177 filed Mar. 14, 2016.

Extended European Search Report issued in corresponding EP application No. 16764059.8 on Nov. 20, 2018.

CN Office Action mailed May 12, 2020 for CN Application No. 201680020190.0.

Examination Report issued in corresponding European Patent Application No. 16764059.8, mailed Dec. 12, 2022, 6 pages.

* cited by examiner

RESPIRATORY THERAPY APPARATUS AND METHOD

1 CROSS-REFERENCE TO RELATED APPLICATIONS

The present application is a national phase entry under 35 U.S.C. § 371 of International Application No. PCT/AU2016/050177 filed Mar. 14, 2016, published in English, which claims priority from Australian Patent Application No. 2015900907 filed Mar. 13, 2015, all of which are incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE TECHNOLOGY

5.1 Field of the Technology

The present technology relates to one or more of the detection, diagnosis, treatment, prevention and amelioration of respiratory-related disorders. The present technology also relates to medical devices or apparatus, and their use.

5.2 Description of the Related Art

5.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

A range of therapies have been used to treat or ameliorate such conditions. Furthermore, otherwise healthy individuals may take advantage of such therapies to prevent respiratory disorders from arising. However, these have a number of shortcomings.

5.2.2 Respiratory Therapies

Respiratory pressure therapy, such as Continuous Positive Airway Pressure (CPAP) therapy, has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall.

By contrast with respiratory pressure therapy, high flow therapy (HFT) does not rely on positive airway pressure delivered to a sealed patient interface, but rather on delivery of air at a therapeutic flow rate to the vicinity of the entrance(s) to the patient's airway via an unsealed patient interface that is significantly open to atmosphere. High flow therapy has been used to treat OSA, CSR, and COPD. One hypothesised mechanism of action is that the air being delivered to the airway at a high flow rate flushes out the patient's anatomical deadspace and decreases the amount of rebreathed $CO_2$, thereby increasing the efficiency of gas exchange.

The delivered high flow rate may be in the range of about 0 to 120 litres/minute, preferably between about 0 and 75 litres/minute, more preferably between about 0 to about 50 litres/minute, with the preferred range being between about 10 to about 35 litres/minute, to provide for comfort and efficacy and to reduce rebreathing.

The delivered air temperature may be in the range of about 0° C. to about 50° C., more preferably about +4° C. to about +45° C., yet more preferably room temperature up to 40° C. with the most preferred range being 30° C. to 37° C., to provide for comfort and efficacy.

The delivered relative humidity of the air may be in the range of room humidity up to 100%, for example in the range of about 50% to about 100%, or about 70% to about 100%, or about 80% to about 95%, with the preferred range being 80% to 90%, to provide for comfort and efficacy. An absolute humidity range may be about 0 to about 82 mg/litre, or more preferably about 27 to about 44 mg/litre.

High flow therapy may be as described in U.S. Patent Application Publication No. 2011-0253136 filed as International Patent Application PCT/AU09/00671 on May 28, 2009, the entire disclosure of which is incorporated herein by cross reference. High flow therapy may be used in conjunction with respiratory pressure therapy.

5.2.3 Treatment Systems

Respiratory therapies may be provided by a treatment system or apparatus. A treatment system may comprise a Respiratory Therapy Device (RT device), an air circuit, a humidifier, a patient interface, and data management.

5.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth, or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. A sealed interface may still have one or more vents to provide gas exhaust to atmosphere. For other forms of therapy, such as high flow therapy, the patient interface may be unsealed, i.e. may not form a seal with the airway entrance. The flow of air may be provided via a cannula to the nose, a tube to the mouth, or a tracheostomy tube to the trachea of a patient. This type of unsealed patient interface when used with high flow therapy essentially permits a significant flow of treatment air to escape to atmosphere at a gap between the interface and the patient's nares. Under such escape-flow conditions, sensing or detection of conditions related to the patient use of therapy and/or the breathing of the patient can be confounded in no small part due to the lack of a pressure controlled environment (e.g. between the patient and cannula interface). Thus, embodiments of the present technology may be implemented to overcome such difficulties to yield a metric for therapy use while still employing traditional sensors.

5.2.3.2 Respiratory Therapy (RT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

One known RT device used for treating sleep disordered breathing is the S9 Sleep Therapy System, manufactured by ResMed Limited. Another example of an RT device is a ventilator. Ventilators such as the ResMed Stellar™ Series of Adult and Paediatric Ventilators may provide support for invasive and non-invasive non-dependent ventilation for a range of patients for treating a number of conditions such as but not limited to CSR and COPD.

RT devices typically comprise a pressure generator, such as a motor-driven blower or a compressed gas reservoir, and are configured to deliver a flow of air to the airway of a patient. The outlet of the RT device is connected via an air circuit to a patient interface such as those described above.

5.2.3.3 Humidifier

Delivery of a flow of air without humidification may cause drying of airways. The use of a humidifier with an RT device and the patient interface produces humidified gas that minimizes drying of the nasal and/or throat mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

5.2.3.4 Data Management

There may be clinical reasons to obtain data to determine whether the patient prescribed with respiratory therapy has been "compliant", e.g. whether the patient has used their RT device according to certain a "compliance rule" associated with the prescribed respiratory therapy. One example of a compliance rule for CPAP therapy is that a patient, in order to be deemed compliant, is required to use the RT device for at least four hours a night for at least 21 of 30 consecutive days. Similar compliance rules may be implemented for high flow therapy. In order to determine a patient's compliance, a provider of the RT device, such as a health care provider, may manually obtain therapy data describing the patient's respiratory therapy using the RT device, estimate/calculate the usage over a predetermined time period, and compare with the compliance rule. Once the health care provider has determined that the patient has used their RT device according to the compliance rule, the health care provider may notify a third party, such as an insurer, that the patient is compliant. There may be other aspects of a patient's therapy that would benefit from communication of therapy data to a third party or external system.

Conventional methods exist for analysing therapy data to determine when a patient is using their RT device to deliver CPAP therapy or other respiratory pressure therapies. However, because of the different pneumatics of high flow therapy resulting from its usually unsealed character, such methods yield inaccurate results if applied to determining whether a patient is using their RT device to deliver high flow therapy. A need therefore exists for methods of and apparatus for determining when an RT device is being, or has been, used for high flow therapy.

6 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

In general, the present technology relates to apparatus and methods used in the diagnosis, amelioration, treatment or prevention of a respiratory disorder.

One form of the present technology comprises apparatus and methods for determining from flow rate and/or pressure signals whether a patient is using, or has used, high flow therapy. The apparatus and methods may look for a significant oscillation in the breathing rate frequency band in one or more of these signals to determine whether the patient is using the high flow therapy.

In accordance with one aspect of the present technology, there is provided a method of determining whether high flow therapy is being used by a patient. The method may include determining, by evaluation of one or more signals in a controller associated with a respiratory therapy device, the one or more signals from one or more sensors, whether a property of a flow of air being delivered by the respiratory therapy device along an air circuit to an unsealed patient interface contains a significant oscillation within a breathing rate frequency band. The method may also include generating, in the controller, dependent on the determining, an output indication of whether high flow therapy is being used by the patient.

In accordance with another aspect of the present technology, there is provided an apparatus for delivering high flow therapy to a patient. The apparatus may include a servo-controlled blower configured to generate a flow of air along an air circuit to an unsealed patient interface at a predetermined therapeutic flow rate. The apparatus may include one or more transducers configured to generate respective signals representing respective properties of the flow of air being generated. The apparatus may include a central controller configured to control the servo-controlled blower. The apparatus may include a processor. The processor may be configured to receive the one or more signals. The processor may be configured to control a determination of whether a property of the flow of air represented by one of the one or more signals contains a significant oscillation within a breathing rate frequency band. The processor may be configured to generate, dependent on the determination, an indication of whether high flow therapy is being used by the patient.

In accordance with another aspect of the present technology, there is provided an apparatus for delivering high flow therapy to a patient. The apparatus may include flow means for generating a flow of air along an air circuit to an unsealed patient interface. The apparatus may include means for controlling the flow means. The apparatus may include means for generating one or more signals representing respective properties of the flow of air being generated. The apparatus may include means for receiving the one or more signals. The apparatus may include means for determining whether a property of the flow of air represented by one of the one or more signals contains a significant oscillation within a breathing rate frequency band. The apparatus may include means for generating, dependent on the determination, an indication of whether high flow therapy is being used by the patient.

In accordance with another aspect of the present technology, there is provided a high flow therapy system. The high flow therapy system may include an unsealed patient interface. The system may include an air circuit configured to be connected to the unsealed patient interface. The system may include a servo-controlled blower configured to generate a flow of air along an air circuit. The system may include a central controller configured to control the servo-controlled blower. The system may include one or more transducers configured to generate one or more signals representing respective properties of the flow of air being generated. The system may include a processor. The processor may be configured to receive the one or more signals. The processor may be configured to control a determination of whether a property of the flow of air represented by one of the one or more signals contains a significant oscillation within a breathing rate frequency band. The processor may be configured to generate, dependent on the determination, an indication of whether high flow therapy is being used by the patient.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE DRAWINGS

The present technology is illustrated by way of example, and not by way of limitation, in the figures of the accompanying drawings, in which like reference numerals refer to similar elements including:

7.1 Treatment Systems

FIG. 1 shows a system including a patient 1000 wearing a patient interface 3000, in the form of nasal pillows, receiving air at positive pressure from an RT device 4000. Air from the RT device is humidified in a humidifier 5000, and passes along an air circuit 4170 to the patient 1000. A bed partner 1100 is also shown.

7.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

7.3 Patient Interface

7.4 Respiratory Therapy Device

Figure 1:
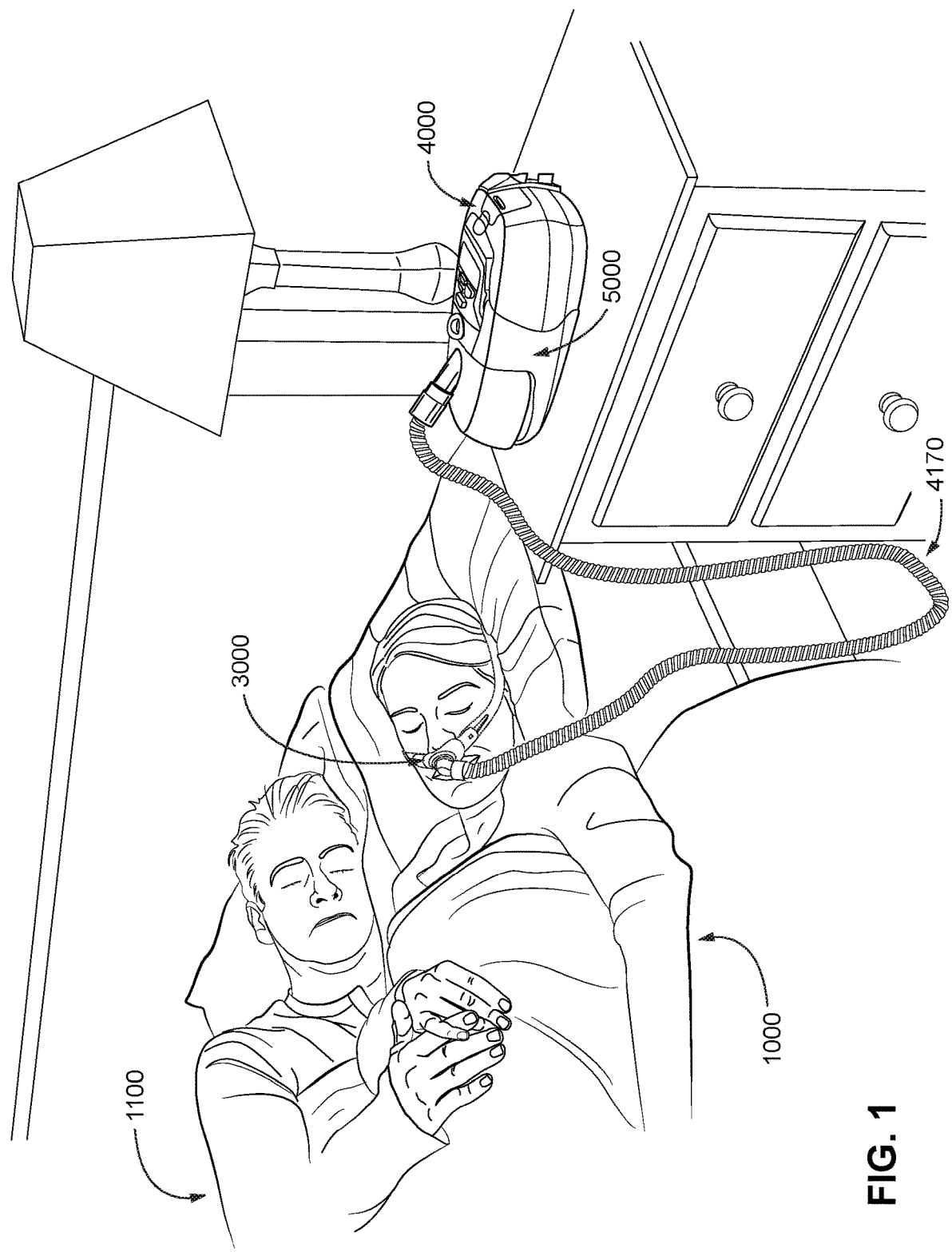
Figure 2:
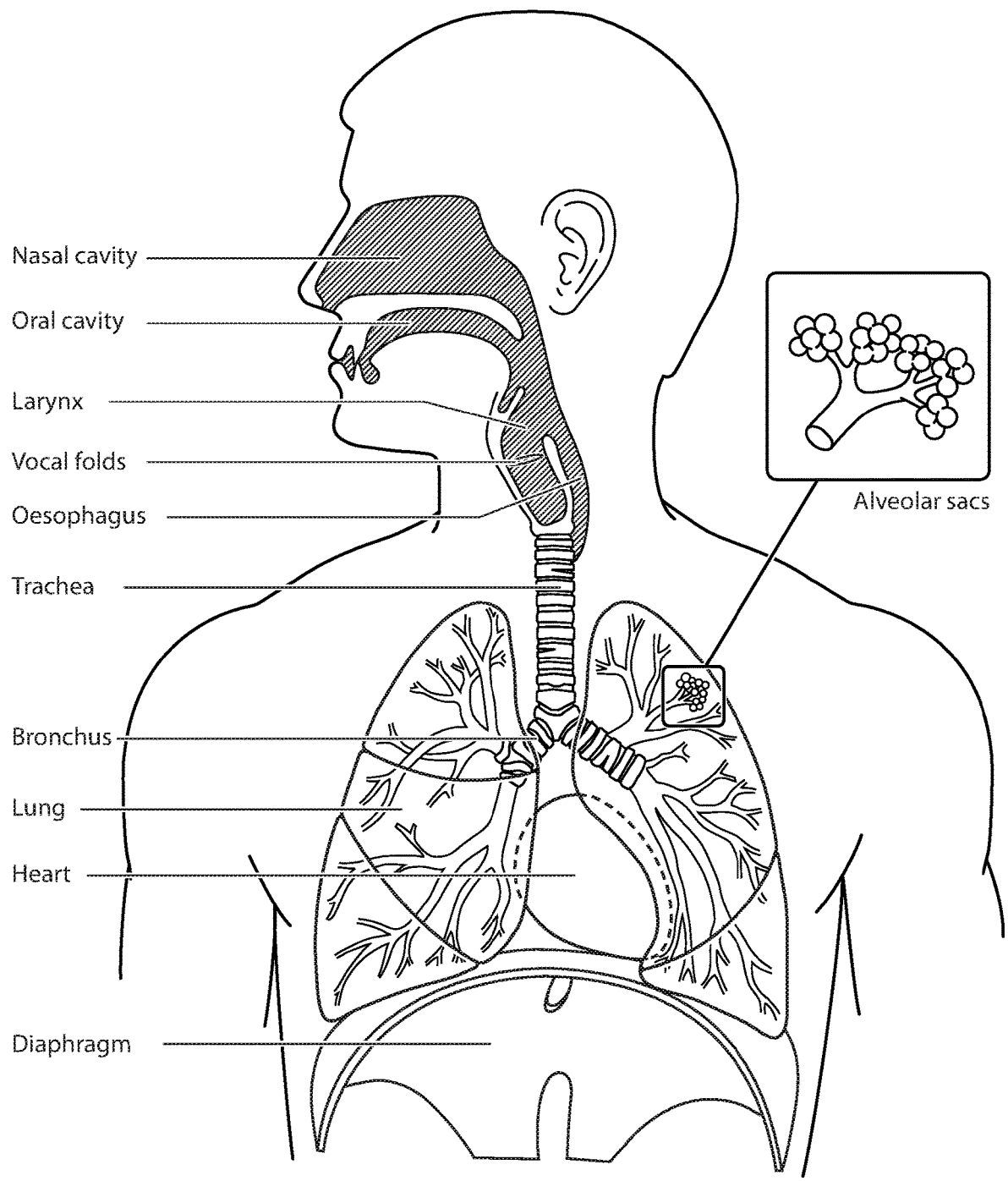
Figure 3A:
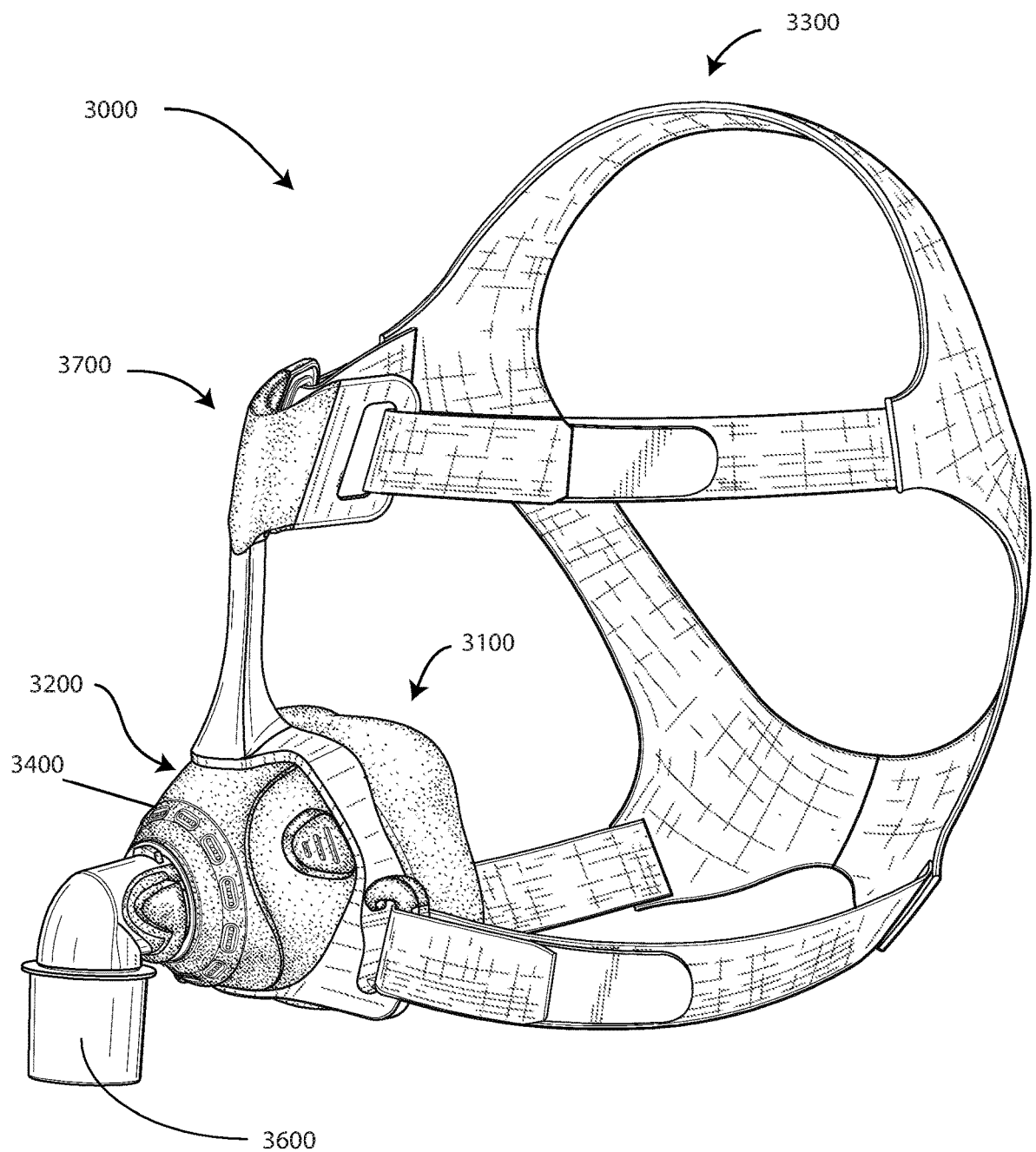
FIG. 3A shows a sealed patient interface 3000 suitable for respiratory pressure therapy.
Figure 3B:
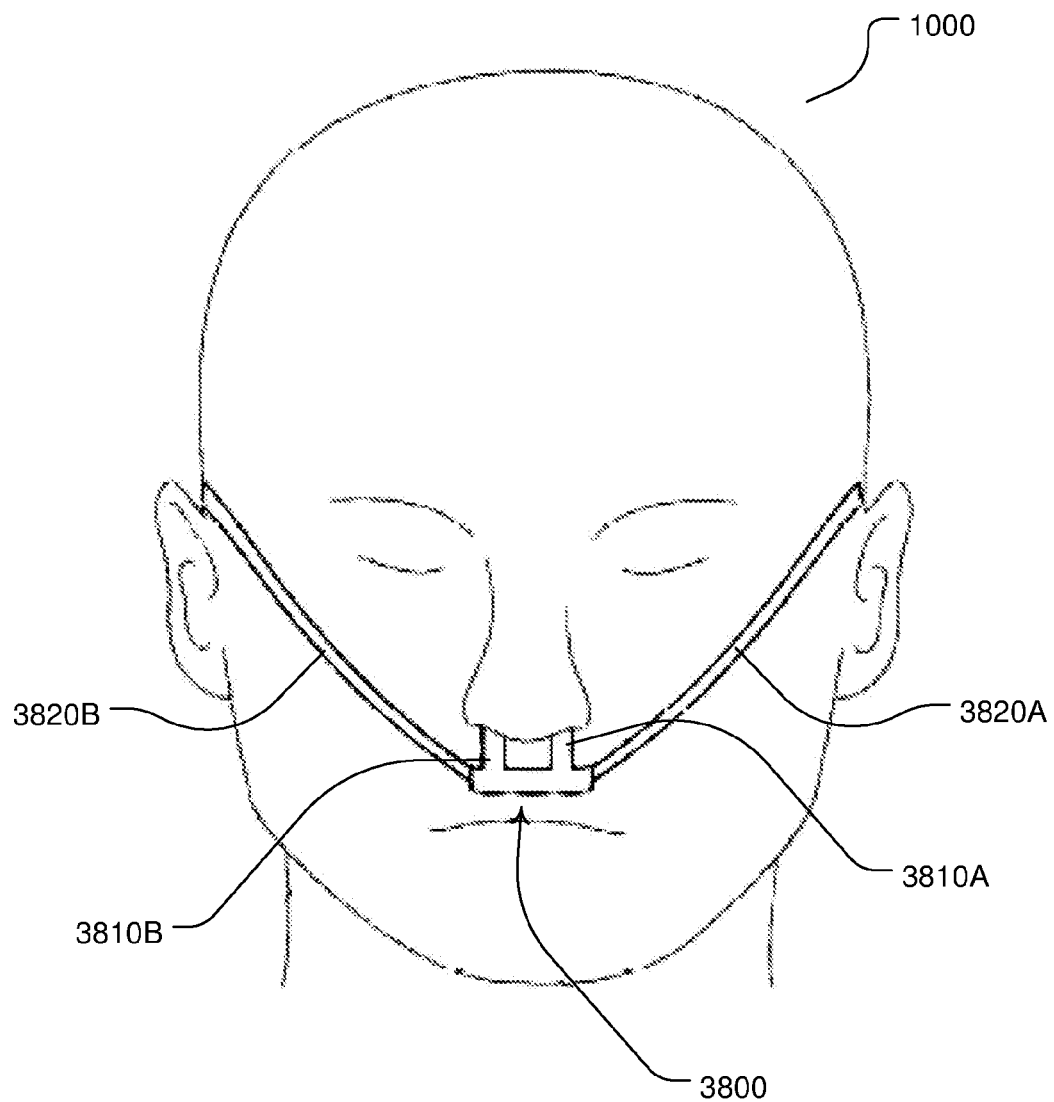
FIG. 3B shows an unsealed patient interface 3800 suitable for high flow therapy, in use on a patient 1000.
Figure 4A:
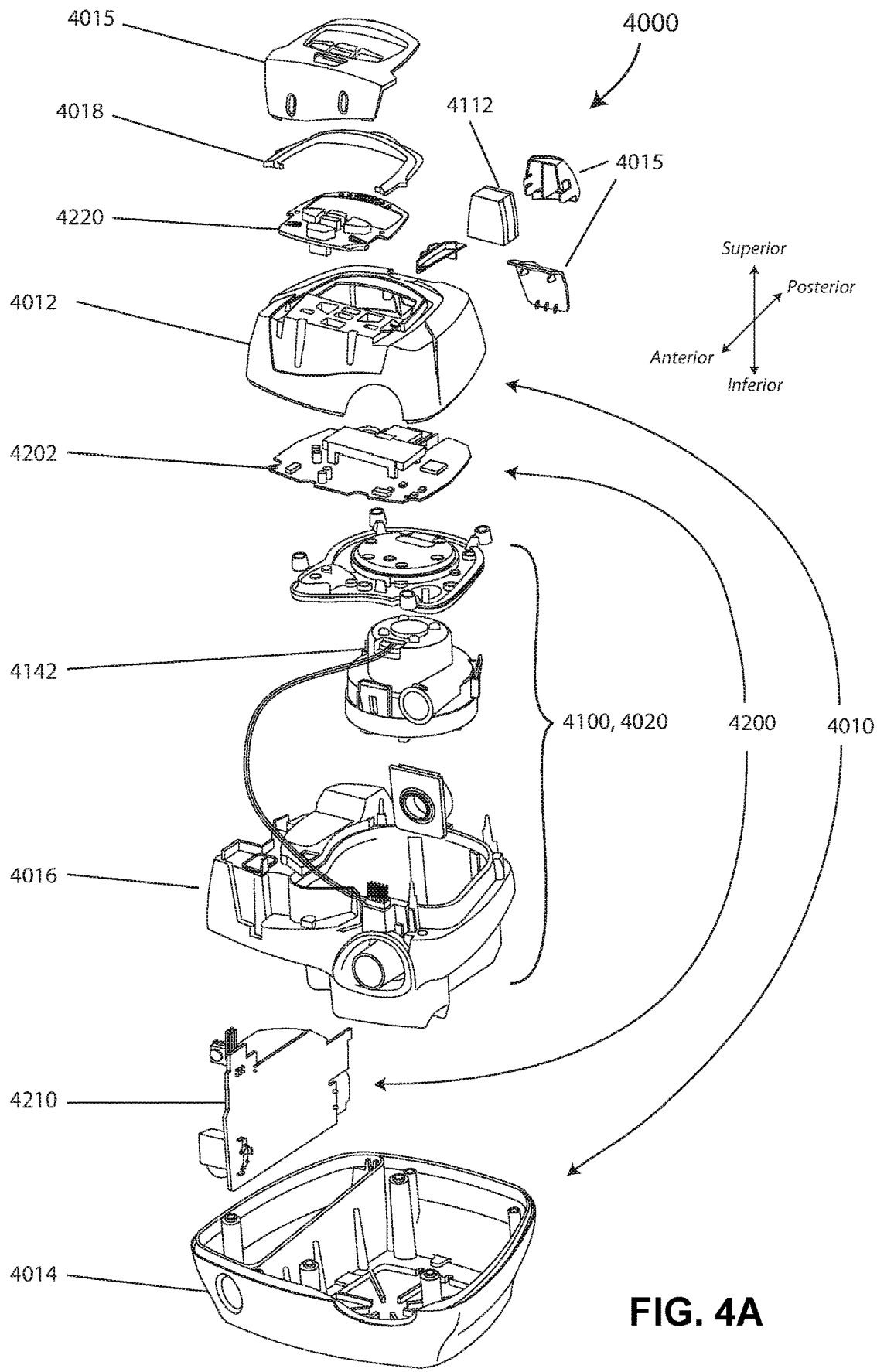

FIG. 4A shows an RT device 4000 in accordance with one form of the present technology.

Figure 4B:
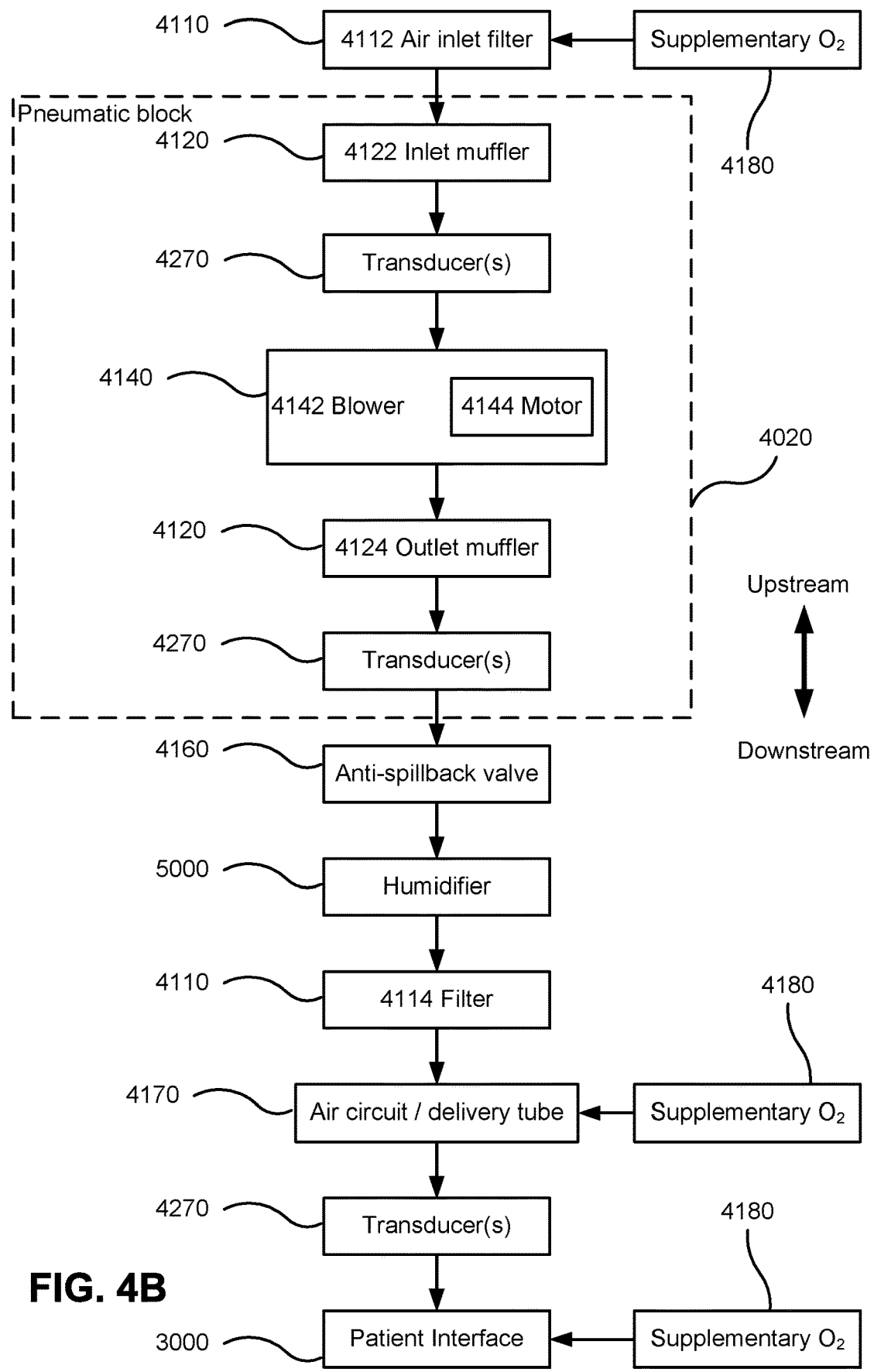

FIG. 4B is a schematic diagram of the pneumatic path of an RT device in accordance with one form of the present technology. The directions of upstream and downstream are indicated.

Figure 4C:
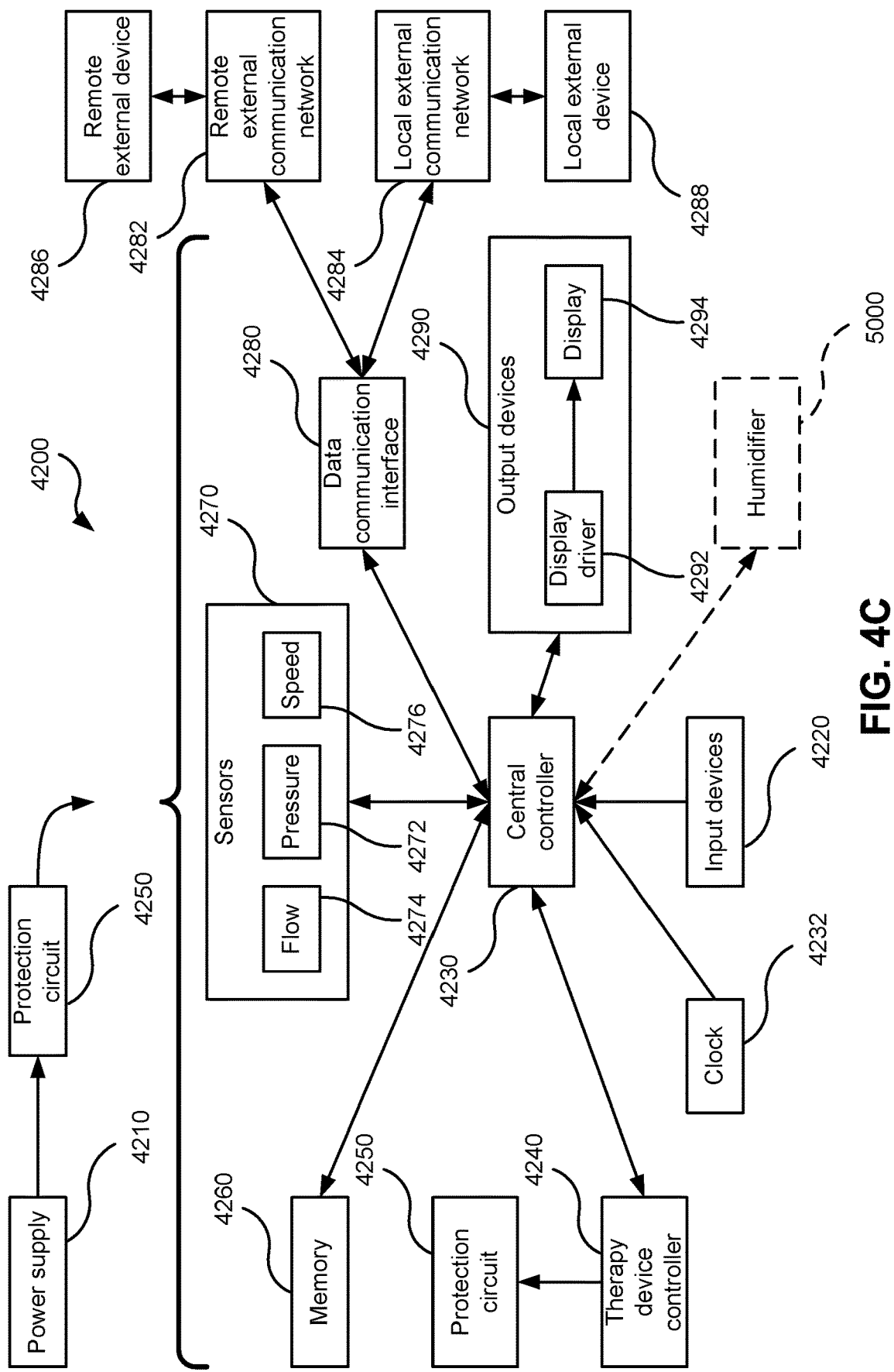

FIG. 4C is a schematic diagram of the electrical components of an RT device in accordance with one form of the present technology.

7.5 Humidifier

Figure 5A:
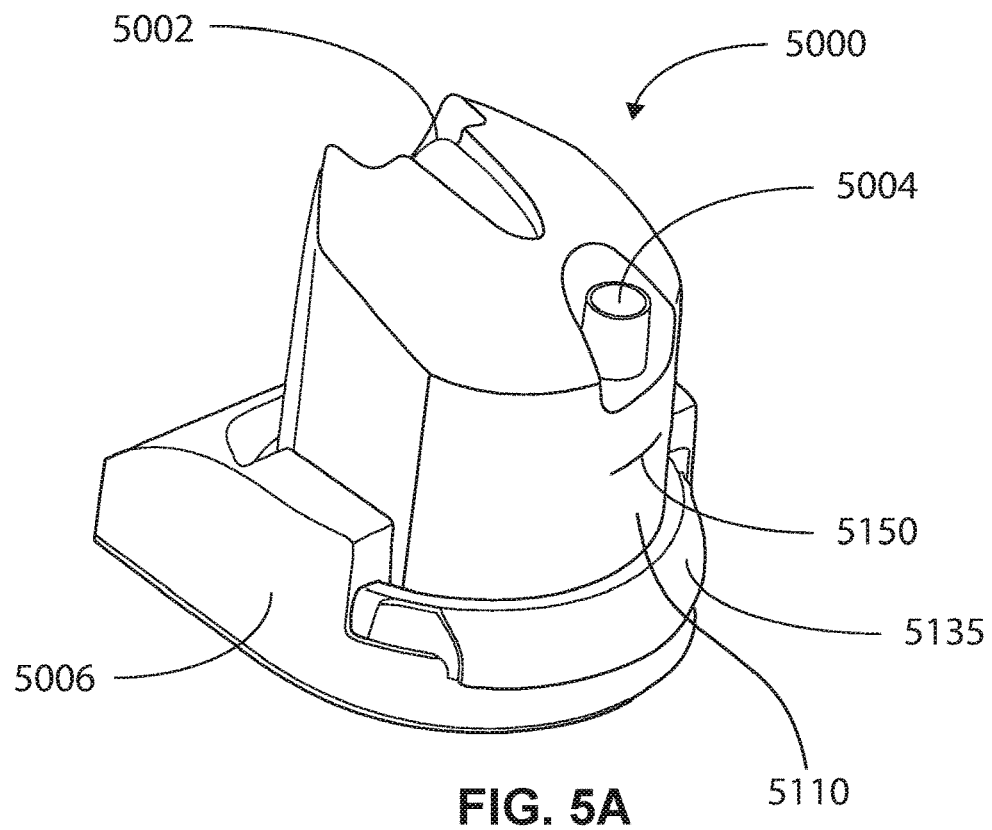

FIG. 5A shows an isometric view of a humidifier 5000.

Figure 5B:
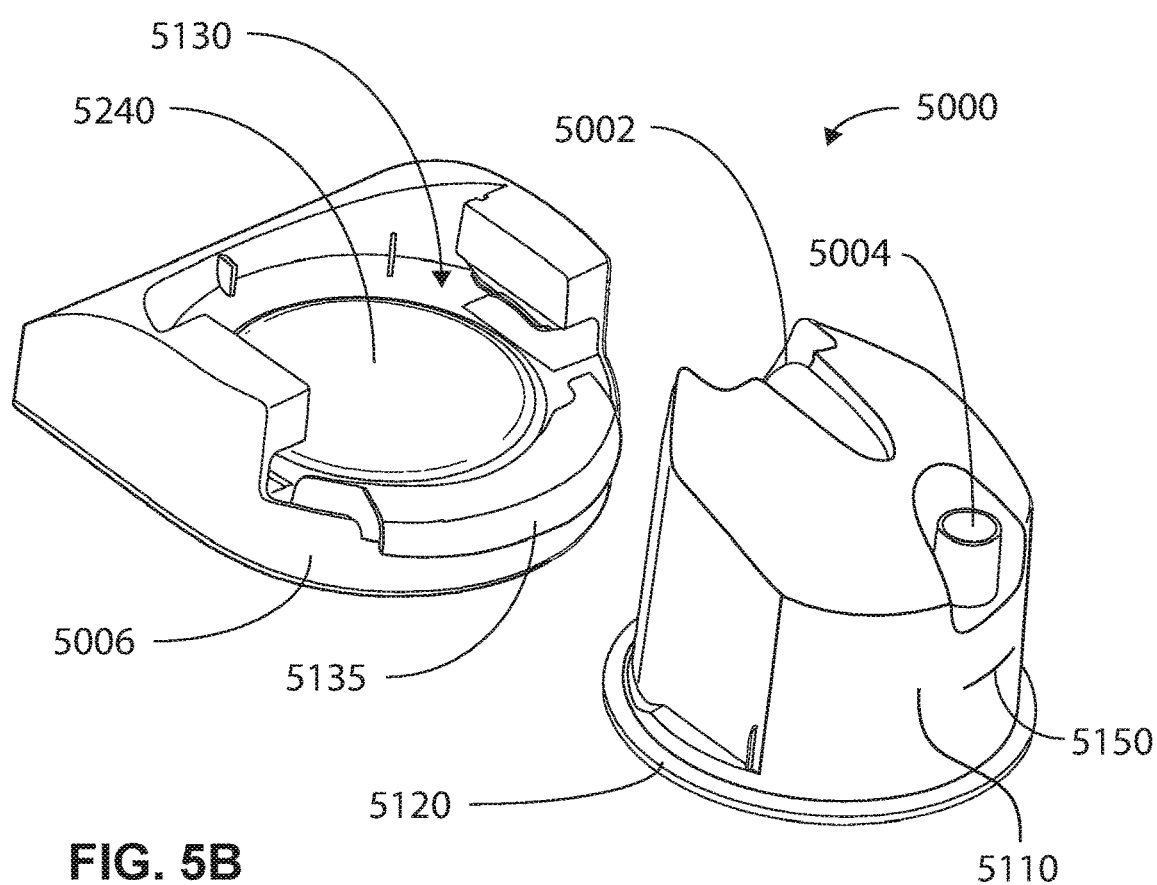

FIG. 5B shows an isometric view of a humidifier, showing a humidifier reservoir 5110 removed from the humidifier reservoir dock 5130.

7.6 Therapy Usage Determination

Figure 6A:
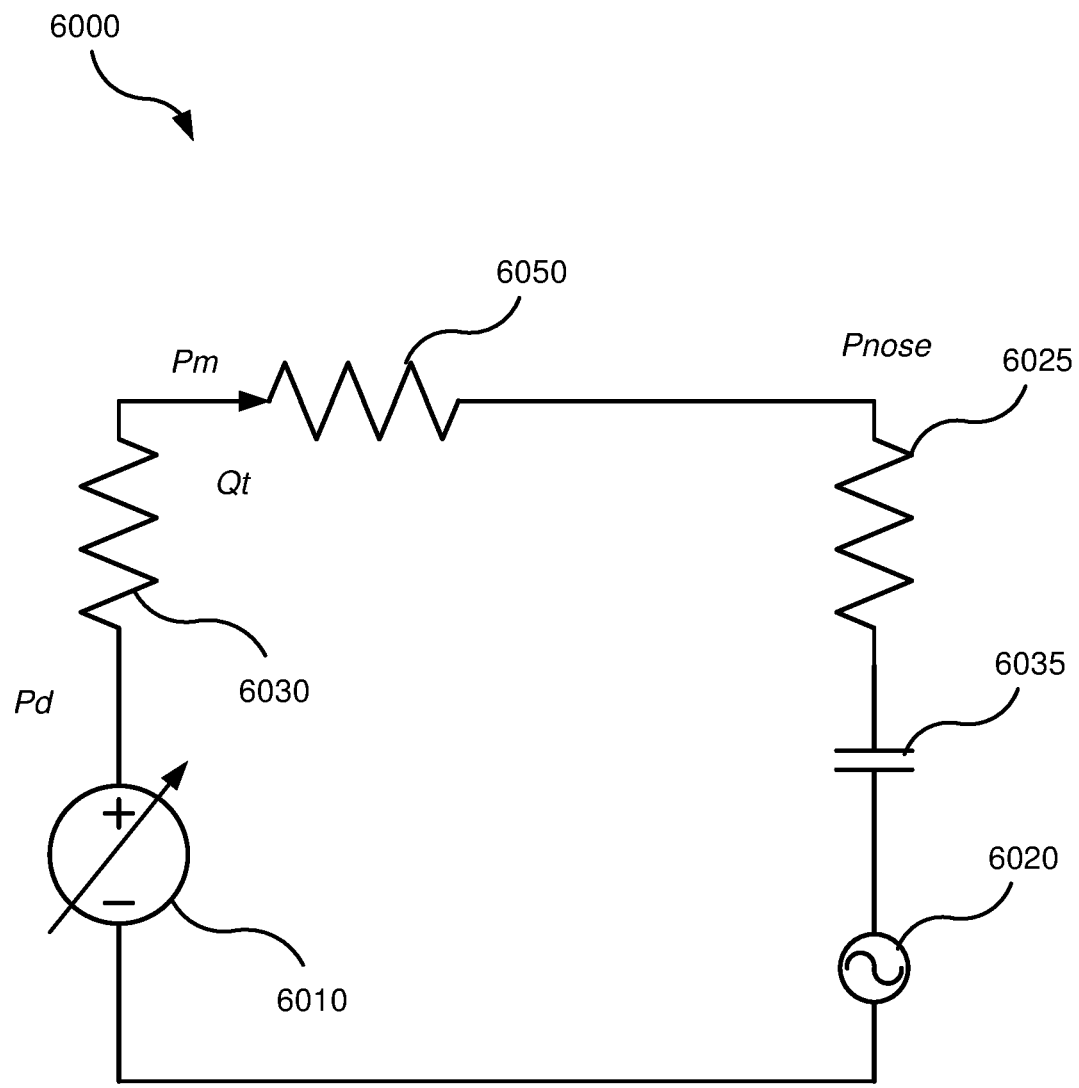

FIG. 6A is a circuit diagram of an electrical circuit that forms a simple model of an RT device delivering high flow therapy to a breathing patient via an unsealed patient interface.

Figure 6B:
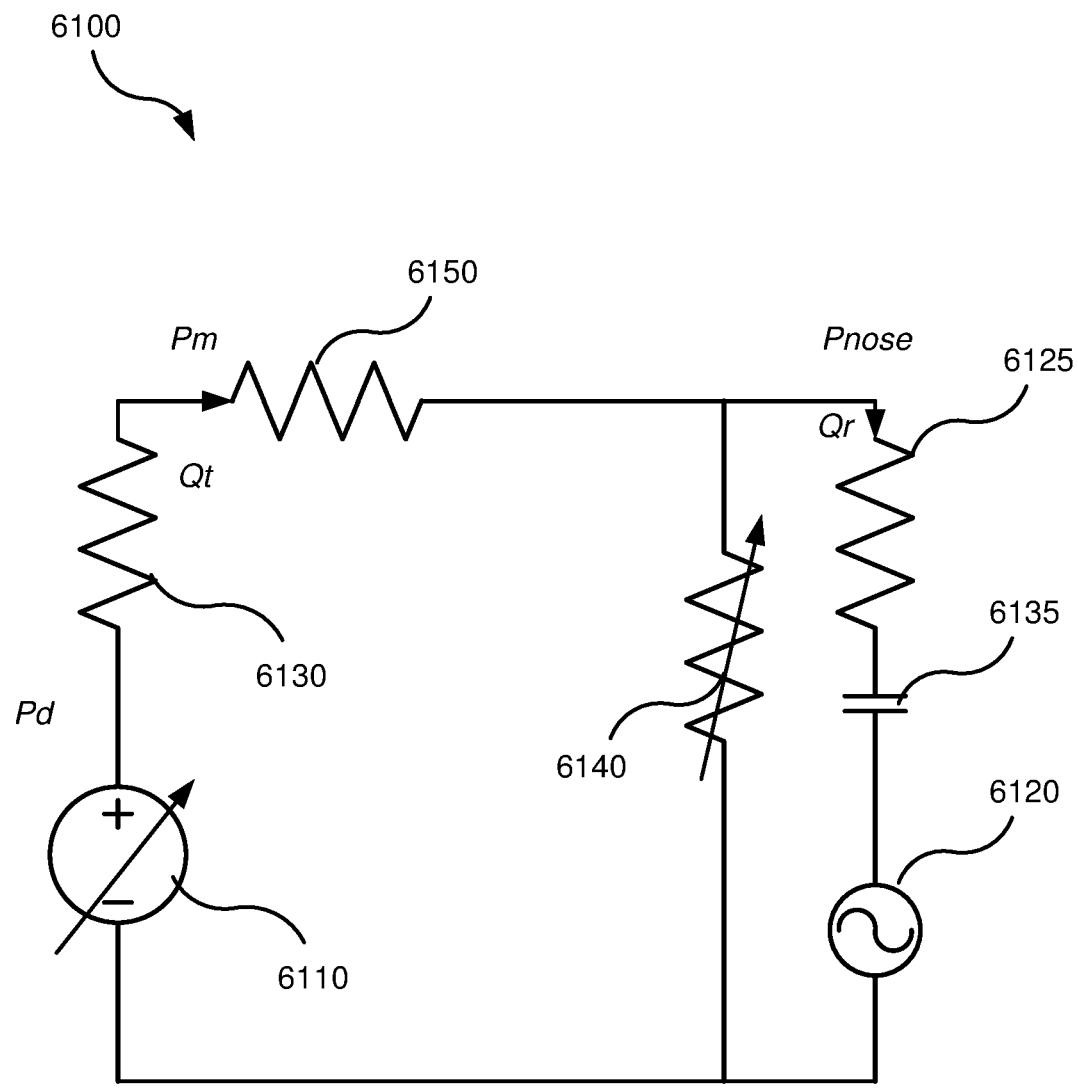

FIG. 6B is a circuit diagram of an electrical circuit that forms a more sophisticated model of an RT device delivering high flow therapy to a breathing patient.

Figure 6C:
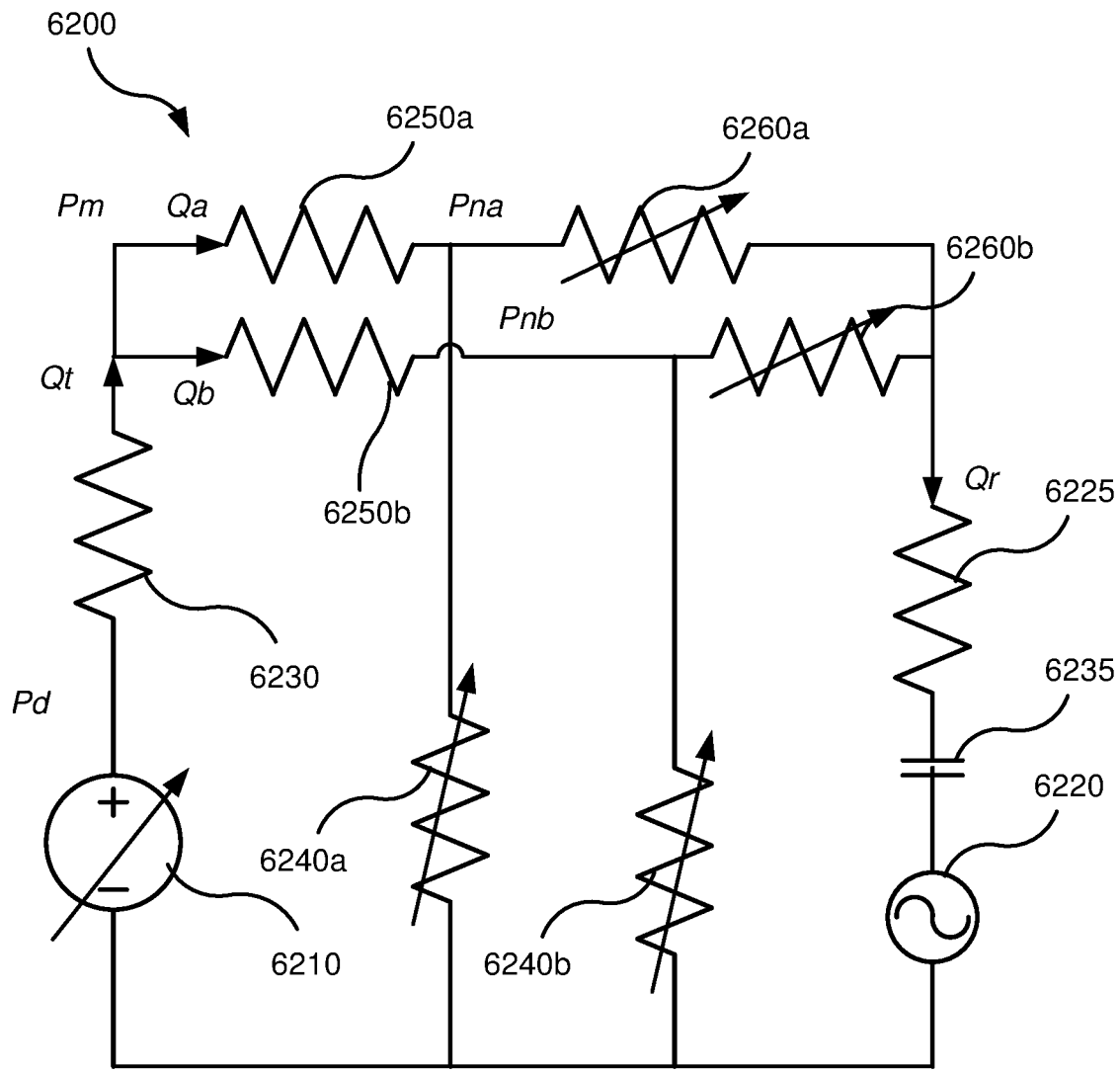

FIG. 6C is a circuit diagram of an electrical circuit that forms a two-nostril model of an RT device delivering high flow therapy to a breathing patient.

Figure 7A:
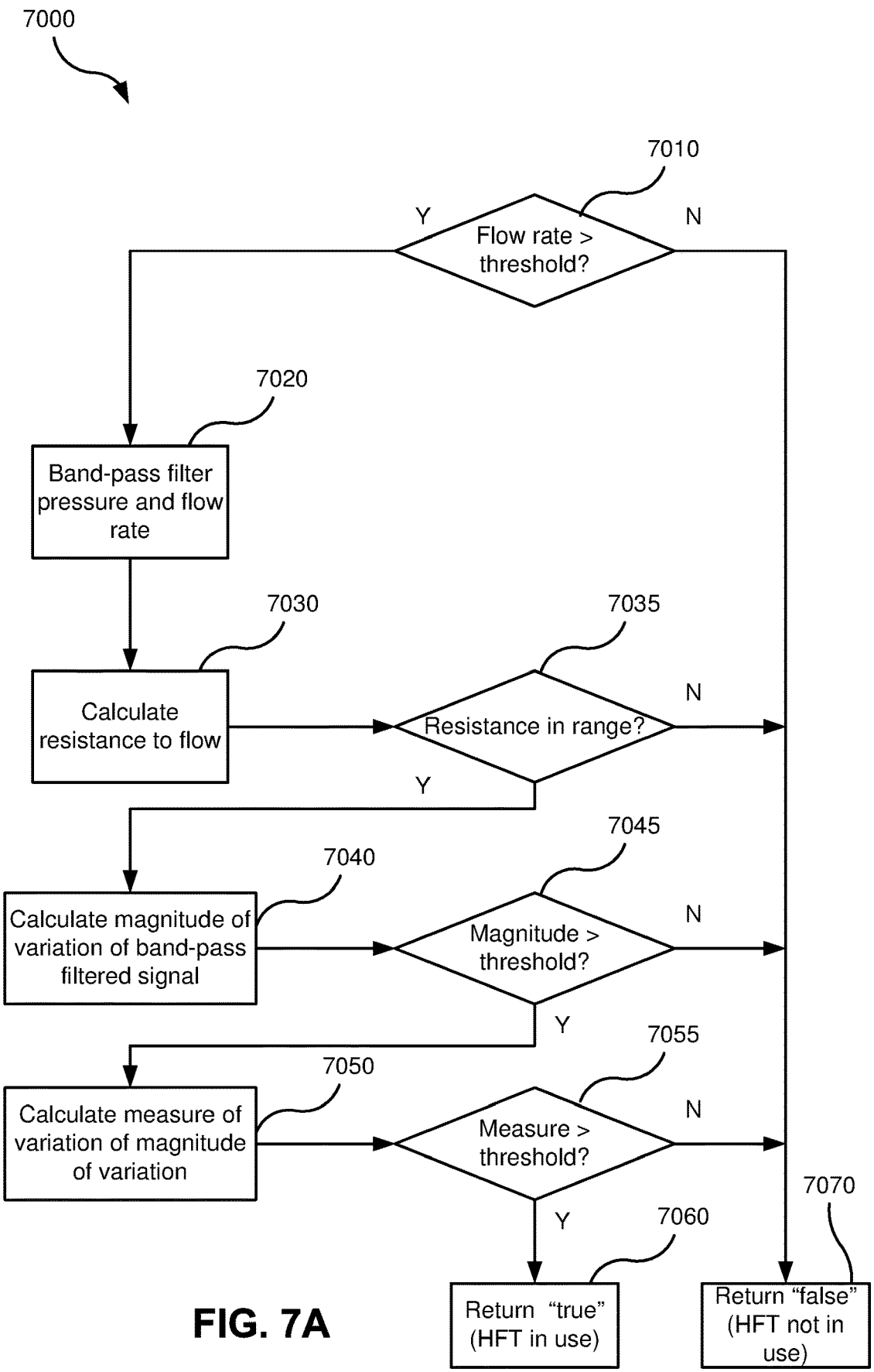

FIG. 7A is a flow chart illustrating a method of determining whether a patient is using high flow therapy, in accordance with one form of the present technology.

Figure 7B:
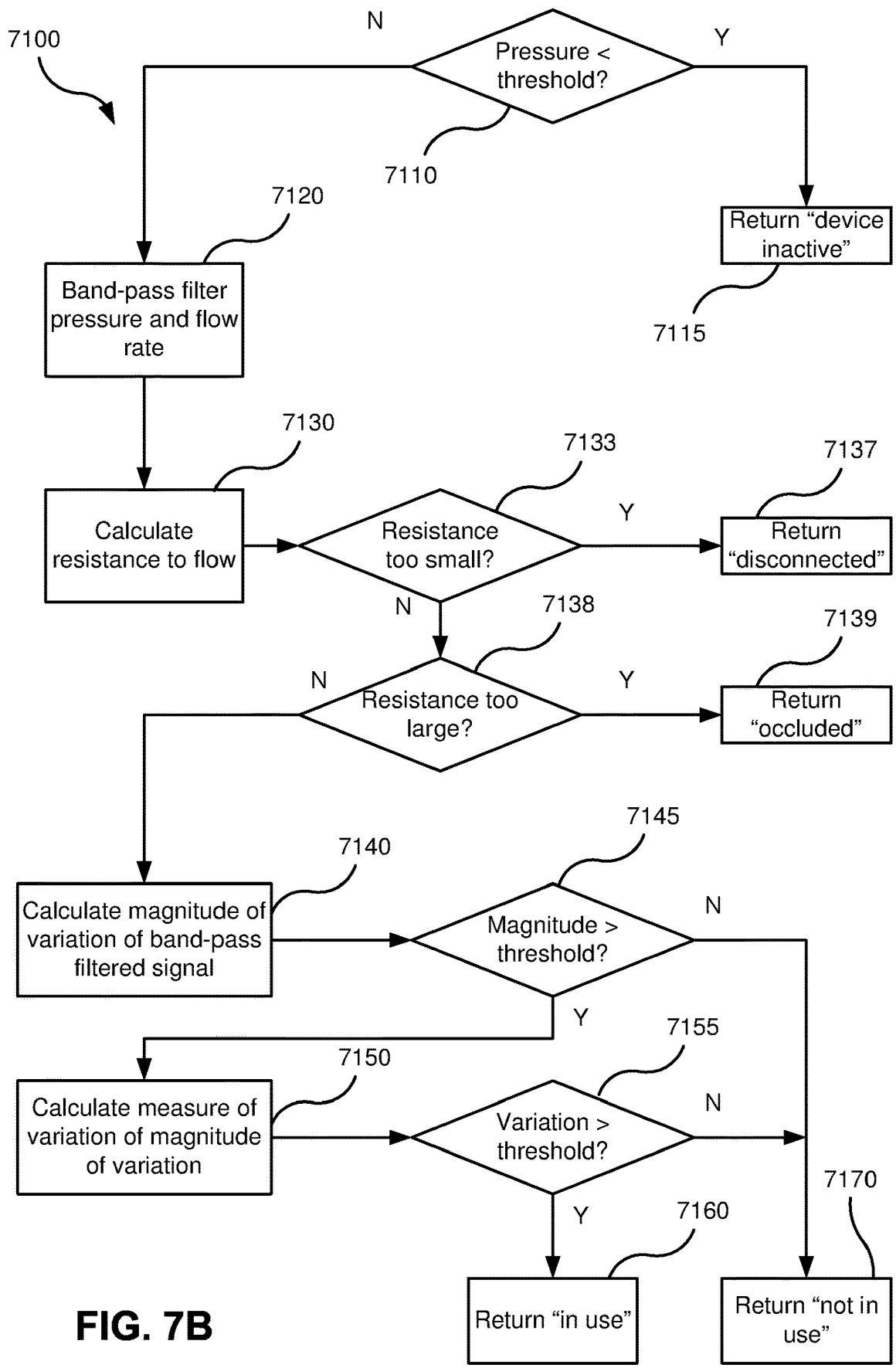

FIG. 7B is a flow chart illustrating a method of monitoring a patient's high flow therapy, in accordance with one form of the present technology.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

8.1 Therapy

In one form, the present technology comprises a method for treating a respiratory disorder comprising the step of delivering a flow of air at high flow rates to the vicinity of an entrance of the airways of a patient 1000.

In certain examples of the present technology, the flow of air at high flow rates is delivered to the nasal passages of the patient via one or both nares.

8.2 Treatment Systems

In one form, the present technology comprises an apparatus or device for treating a respiratory disorder. The apparatus or device may comprise an RT device 4000 for delivering air at high flow rates to the patient 1000 via an air circuit 4170 to an unsealed patient interface 3800.

8.3 Patient Interfaces

A non-invasive sealed patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In use the seal-forming structure 3100 is arranged to surround an entrance to the airways of the patient so as to facilitate the supply of air at positive pressure to the airways.

An unsealed patient interface 3800, in the form of a nasal cannula, includes nasal prongs 3810a, 3810b which can deliver air to respective nares of the patient 1000. Such nasal prongs do not generally form a seal with the inner or outer skin surface of the nares. The air to the nasal prongs may be delivered by one or more air supply lumens 3820a, 3820b that are coupled with the nasal cannula form of the unsealed patient interface 3800. The lumens 3820a, 3820b lead from the nasal cannula form of the unsealed patient interface 3800 lead to an RT device that generates the flow of air at high flow rates.

Another example of an unsealed patient interface 3800 is a trans-tracheal interface.

8.4 Respiratory Therapy Device

An RT device 4000 in accordance with one aspect of the present technology comprises mechanical and pneumatic components 4100, electrical components 4200 and is configured to execute one or more algorithms 4300. The RT device may have an external housing 4010, formed in two parts, an upper portion 4012 and a lower portion 4014. Furthermore, the external housing 4010 may include one or more panel(s) 4015. The RT device 4000 comprises a chassis 4016 that supports one or more internal components of the RT device 4000. The RT device 4000 may include a handle 4018.

The pneumatic path of the RT device 4000 may comprise one or more air path items, e.g., an inlet air filter 4112, an inlet muffler 4122, a pressure generator 4140 capable of delivering air at high flow rates (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RT device 4000 may include more than one PCBA 4202.

8.4.1 RT Device Mechanical & Pneumatic Components

An RT device may comprise one or more of the following components in an integral unit. In an alternative form, one or more of the following components may be located as respective separate units.

8.4.1.1 Air Filter(s)

An RT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface.

8.4.1.2 Muffler(s)

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface.

8.4.1.3 Pressure Generator

In one form of the present technology, a pressure generator 4140 for producing a flow of air at high flow rates is a servo-controlled blower 4142. For example the blower 4142 may include a brushless DC motor 4144 with one or more impellers housed in a volute. The blower 4142 may be servo-controlled to deliver a flow of air at a therapeutic flow rate Qth. In such an implementation, the total flow rate Qt of the air flow is monitored by a flow rate transducer as described below and the speed of the blower 4142, and thereby the pressure Pd of the air flow at the output of the blower 4142, is adjusted so as to maintain the total flow rate Qt at or about the therapeutic flow rate Qth. The therapeutic flow rate Qth may be as high as about 120 litres/minute, but more typically is in the range of 20 to 30 litres/minute.

The blower 4142 may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

8.4.1.4 Transducer(s)

Transducers 4270 may be internal of the RT device, or external of the RT device. External transducers may be located for example on or form part of the air circuit, e.g., the patient interface. External transducers may be in the form of non-contact sensors such as a Doppler radar movement sensor that transmit or transfer data to the RT device.

In one form of the present technology, one or more transducers 4270 are located upstream and/or downstream of the pressure generator 4140. The one or more transducers 4270 may be constructed and arranged to measure properties such as flow rate, pressure, absolute or relative humidity, or temperature at a point in the pneumatic path. The transducers 4270 generate signals representing the properties and transmit the signals to the central controller 4230.

In one form of the present technology, one or more transducers 4270 may be located proximate to the patient interface. In another form of the present technology, one or more transducers 4270 may be located proximate to the air outlet of the RT device 4000. External transducers may also be used to measure the ambient conditions, e.g. ambient pressure, temperature, or relative or absolute humidity.

In one form, a signal from a transducer 4270 may be filtered, such as by low-pass, high-pass or band-pass filtering.

8.4.1.4.1 Flow Rate Transducer

A flow rate transducer 4274 in accordance with the present technology may be based on a differential pressure transducer, for example, an SDP600 Series differential pressure transducer from SENSIRION.

In one form, the flow rate transducer 4274 generates a signal representing the total flow rate Qt of the air flow being delivered by the RT device 4000.

8.4.1.4.2 Pressure Transducer

A pressure transducer 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, the pressure transducer 4272 generates a signal representing the pressure Pd of the air flow at the outlet of the RT device 4000.

8.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

8.4.1.4.4 Other Transducers

One or more humidity/temperature sensors such as a Sensirion SHT75 may be used to determine humidity and temperature of the therapeutic flow of air as well as ambient humidity and temperature.

One or more electrical sensors may be configured to sense the current consumed by the motor 4144 or humidifier 5000 or their respective power supply units. The sensed current may be used to determine the instantaneous or average power being consumed by the treatment system, or components thereof.

8.4.1.5 Anti-Spill Back Valve

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

8.4.1.6 Air Circuit

An air circuit 4170 in accordance with an aspect of the present technology is a conduit or a tube constructed and arranged in use to allow a flow of air to travel between two components such as the pneumatic block 4020 and the patient interface.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230 or a humidifier controller 5250. One example of an air circuit 4170 comprising a heated wire circuit is described in United States Patent Application No. US/2011/0023874, which is incorporated herewithin in its entirety by reference.

8.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface.

8.4.2 RT Device Electrical Components

8.4.2.1 Power Supply

A power supply 4210 may be located internal or external of the external housing 4010 of the RT device 4000.

In one form of the present technology power supply 4210 provides electrical power to the RT device 4000 only. In another form of the present technology, power supply 4210 provides electrical power to both RT device 4000 and humidifier 5000.

8.4.2.2 Input Devices

In one form of the present technology, an RT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

8.4.2.3 Central Controller

In one form of the present technology, the central controller 4230 is one or a plurality of processors suitable to control an RT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier controller 5250.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RT device 4000. However, in some forms of the present technology, some methodologies may be performed by a remotely located device. For example, the remotely located device may determine control settings for a ventilator or detect respiratory related events by analysis of stored data such as from any of the sensors described herein.

8.4.2.4 Clock

The RT device 4000 may include a clock 4232 that is connected to the central controller 4230.

8.4.2.5 Therapy Device Controller

In one form of the present technology, therapy device controller 4240 is a control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

8.4.2.6 Protection Circuits

The one or more protection circuits 4250 in accordance with the present technology may comprise an electrical protection circuit, a temperature and/or pressure safety circuit.

8.4.2.7 Memory

In accordance with one form of the present technology the RT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

8.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol, or power line communication.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

The local external device 4288 may be a personal computer, mobile phone, tablet or remote control.

8.4.2.9 Output Device

An output device 4290 in accordance with the present technology may take the form of one or more of a visual, audio and haptic unit. A visual display may be a Liquid Crystal Display (LCD) or Light Emitting Diode (LED) display.

8.4.2.9.1 Display Driver

A display driver 4292 receives as an input the characters, symbols, or images intended for display on the display 4294, and converts them to commands that cause the display 4294 to display those characters, symbols, or images.

8.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

8.4.2.9.3 Alarm

An output device 4290 may take the form of an alarm generator. An alarm may take the form of a visual indicator (e.g. a flashing light) or audio signal (e.g. a beep).

8.4.3 RT Device Algorithms

8.4.3.1 High Flow Therapy Usage Determination

The present technology presents improvement(s) in the technical field of respiratory therapy, and in particular, with respiratory therapy apparatus. For example, it can enable an apparatus to automatically determine a status associated with patient use of high flow therapy where an unsealed patient interface is employed. Such determination(s) may be made in a processor, and as such, present improvement(s) in the functioning of a controller or processor. For example, in one form of the present technology, a high flow therapy usage determination algorithm receives as inputs a signal representing the pressure Pd at the RT device outlet, and a signal representing the total flow rate Qt of air being delivered by the RT device 4000. The high flow therapy usage determination algorithm generates as an output a time series of Boolean usage indications of whether high flow therapy is being used by the patient 1000 at successive time instants.

In one form of the present technology, the central controller 4230 of the RT device 4000 may carry out the high flow therapy usage determination algorithm.

In other forms of the present technology, the high flow therapy usage determination algorithm may be carried out by a processor of the remote external computing device 4286 that is configured to communicate with the RT device 4000 via the remote external communication network 4282. In such forms, the RT device 4000 may send signals representing device pressure Pd and the total flow rate Qt to the remote external computing device 4286 via the remote external communication network 4282. The remote external computing device 4286 then implements the high flow therapy usage determination algorithm.

In yet other forms, the high flow therapy usage determination algorithm may be carried out partly by the central controller 4230 of the RT device 4000, and partly by a processor of the remote external computing device 4286. For example, the central controller 4230 may process the device pressure and total flow rate signals to generate intermediate outputs, and transmit the intermediate outputs to the processor of the remote external computing device 4286, which may in turn process the intermediate outputs to generate the time series of usage indications.

In any case, the high flow therapy usage determination algorithm may be carried out in "real time", or as a post-process, that is, after the completion of a therapy session, on stored data representing the device pressure Pd and total flow rate Qt. For post-processing implementations, the device pressure and flow rate data may be stored as a time series of samples at a predefined sampling rate on the memory 4260 of the RT device 4000, and/or on a memory of the remote external computing device 4286.

The device pressure and total flow rate signals are generated by an appropriately positioned pressure transducer 4272 and flow rate transducer 4274 respectively. In an alternative form of the present technology, the high flow therapy usage determination algorithm receives as one input a signal indicative of the pressure Pm within the patient interface. The patient interface pressure Pm may be generated directly by an appropriately positioned pressure transducer 4272, or computed from the device pressure Pd by a pressure compensation algorithm that also takes as input the total flow rate Qt. The pressure compensation algorithm estimates the pressure drop through the air circuit 4170 using the total flow rate Qt and subtracts the estimated pressure drop from the device pressure Pd to compute the patient interface pressure Pm.

The RT device 4000 may accumulate the usage indications generated by the high flow therapy usage determination algorithm into a record of high flow therapy usage over time by the patient 1000. The RT device 4000 may take different actions based on such a record of usage. One example of such an action is to generate a compliance report summarising the high flow therapy usage by the patient 1000 over a given time interval. Such a report may be forwarded over a remote external communication network 4282 to a remote external computing device 4286 associated with a health care provider, for example.

In another example, the therapy control module 4330 of the RT device 4000 may adjust one or more parameters of the high flow therapy, e.g. the therapeutic flow rate Qth, in response to the record of usage of high flow therapy. For example, if the record of usage indicates a declining amount of usage over time, the therapeutic flow rate Qth may be decreased in order to encourage more usage of the high flow therapy. Thus, in some cases, the usage indication or the accumulated record may be evaluated in the controller to serve as a trigger to change an operation of the controller of the RT device 4000. By way of further example, the controller may discontinue treatment (e.g., reducing flow generation or stopping flow generation such as by modifying a control operation of the blower motor) when a sufficient usage indication is met (e.g., a certain time threshold has been satisfied) or the usage indication indicates that the device is not being used at all.

The RT device 4000 may generate an alarm (through the output device 4290) based on the usage indication or the accumulated record thereof. For example, the RT device 4000 may generate an alarm if the accumulated record indicates that the patient 1000 has ceased using high flow therapy for longer than a predetermined interval. Such an alarm may, for example, be an output of the RT device 4000 such as an activation of a sound generator or speaker of the RT device 4000 or other sound generator or speaker of a device in communication with the RT device 4000 or activation of an output warning light of a display 4294 of the RT device 4000 or other display of a local or remote external device 4288 or 4286 in communication with the RT device 4000.

FIG. 6A is a circuit diagram of an electrical circuit model 6000 that is a simple model of an RT device 4000 delivering high flow therapy to a breathing patient 1000 via an unsealed patient interface, e.g. the unsealed patient interface 3800. In the electrical circuit model 6000, voltage models pressure and current models flow rate. The RT device 4000 is modelled by a controlled voltage source 6010. The air circuit 4170 is modelled by a resistance 6030. The total flow rate Qt is modelled by the current in the air circuit resistance 6030, and the device pressure Pd is modelled by the voltage at the output of the voltage source 6010. The pressure Pm within the unsealed patient interface 3800 is modelled by the voltage at the end of the air circuit resistance 6030. If the air circuit 4170 is occluded, the air circuit resistance 6030 is infinite, i.e. an open circuit. The resistance between the interior of the unsealed patient interface 3800 and the interior of the patient's nose is modelled by the interface resistance 6050. The pressure Pnose within the patient's nose is modelled by the voltage at the end of the interface resistance 6050.

The respiratory system of the patient 1000 is modelled by an airway resistance 6025 in series with a capacitance 6035 and an AC voltage source 6020. The capacitance 6035 models the pneumatic compliance of the patient's lungs. The AC voltage source 6020 models the respiration of the patient 1000 by oscillating between a small negative voltage during the inspiratory portion of the breathing cycle, and a small positive voltage during the expiratory portion of the breathing cycle.

FIG. 6B is a circuit diagram of an electrical circuit model 6100 that is a more sophisticated model of an RT device 4000 delivering high flow therapy to a breathing patient 1000 via an unsealed patient interface 3800 than the electrical circuit model 6000 of FIG. 6A. The electrical circuit model 6100 contains elements 6110, 6120, 6125, 6130, 6135, and 6150 that are the same as their respective counterparts 6010, 6020, 6025, 6030, 6035, and 6050 in the electrical circuit model 6000. The circuit model 6100 also contains an additional "leak resistance" 6140 to ground in parallel with the model 6025/6010 of the patient 1000. The leak resistance 6140 models the leak path from the interior of the patient's nose to ambient, due to the gap between the unsealed patient interface 3800 and the entrance(s) to the airway(s) of the patient 1000 to which the unsealed patient interface 3800 is configured to interface. The presence of the leak resistance 6140, which is small compared with the patient airway resistance 6125, makes the total flow rate Qt significantly different from the patient respiratory flow rate Qr, which is modelled as the current in the airway resistance 6125. This contrasts with the more conventional sealed or pressurised system used to deliver respiratory pressure therapy, in which the leak resistance 6140 is replaced by a much larger impedance that models the flow of air to ambient through a vent 3400 while the interface is properly seated on the patient's face. In such a system, there is a big difference in the static pressures in the system between when the patient is using the respiratory pressure therapy and when the interface is disconnected from the patient, when the impedance to ambient falls dramatically. Thus, detecting from the static pressures when the patient is using the respiratory pressure therapy is straightforward.

The leak resistance 6140 depends on the position of the unsealed patient interface 3800 in relation to the airway entrance(s), which is not precisely predictable, so the leak resistance 6140 is modelled as variable. If the unsealed patient interface 3800 is disconnected from the patient's airway entrance, the leak resistance is very low, i.e. close to a short circuit.

In one implementation, the controlled voltage source 6110 is servo-controlled to maintain the total flow rate Qt at or around the therapeutic flow rate Qth as the AC voltage source 6120 output voltage oscillates over the breathing cycle (modelling patient respiration). In one implementation of the servo-control, the device pressure Pd oscillates around a steady-state (DC) pressure at the breathing rate of the patient 1000 in phase with the output of the AC voltage source 6120, i.e. lower during the inspiratory portion and higher during the expiratory portion, and the total flow rate Qt remains constant at the therapeutic flow rate Qth throughout the breathing cycle. This implementation may also be modelled by replacing the controlled voltage source 6110 with a constant current source supplying current Qth. In another implementation of servo-control, the device pressure Pd remains constant throughout the breathing cycle, and the total flow rate Qt oscillates about the therapeutic flow rate Qth at the breathing rate of the patient 1000 in antiphase with the output of the AC voltage source 6120, i.e. higher than the therapeutic flow rate Qth during the inspiratory portion (when the AC voltage is negative) and lower than the therapeutic flow rate Qth during the expiratory portion (when the AC voltage is positive). In other, intermediate implementations of servo-control, the total flow rate Qt oscillates slightly about the therapeutic flow rate Qth at the breathing rate of the patient 1000 in antiphase with the output of the AC voltage source 6120, i.e. slightly higher than the therapeutic flow rate Qth during the inspiratory portion and slightly lower than the therapeutic flow rate Qth during the expiratory portion. Meanwhile, the device pressure Pd oscillates slightly around the steady-state pressure in phase with the output of the AC voltage source 6120, i.e. slightly lower during the inspiratory portion and slightly higher during the expiratory portion. In practice, regardless of the implementation, because of the imperfection of the transducers 4270 used to implement the servo-control, there will be a slight but non-zero oscillation at the breathing rate in both the device pressure Pd and the total flow rate Qt. The implementation of the servo-control determines whether the oscillation appears mainly in the device pressure Pd, mainly in the total flow rate Qt, or is shared between both signals.

One aim of the disclosed high flow therapy usage determination algorithm is to detect these oscillations of device pressure Pd and/or total flow rate Qt within a breathing rate frequency band that result from a patient 1000 using high flow therapy. It is advantageous for the detection to be substantially independent of the implementation of the servo-control, since that implementation is not necessarily known to the disclosed high flow usage determination algorithm. Such oscillations would not be present if the patient 1000 were not using high flow therapy, e.g. if the air circuit 4170 were either occluded or disconnected from the patient's airway entrance.

FIG. 7A is a flow chart illustrating a method 7000 that may be used to implement the high flow therapy usage determination algorithm in accordance with one form of the present technology. The method 7000 is described below in terms of the device pressure Pd. However, the method 7000 works effectively using the patient interface pressure Pm, provided appropriate thresholds are set.

The method 7000 starts at step 7010, which determines whether the total flow rate Qt is greater than a flow rate threshold. In one implementation, the flow rate threshold is 10 litres/minute. Step 7010 is intended to determine whether or not the RT device 4000 is delivering a flow of air at a high flow rate. Reasons for a high flow rate not being delivered include the pressure generator 4140 not being operational or malfunctioning, or the air circuit 4170 or the unsealed patient interface 3800 being obstructed or occluded. If the total flow rate Qt is not greater than the flow rate threshold ("N"), the method 7000 proceeds to the step 7070, which returns a value of "false", indicating that high flow therapy is not being used by the patient 1000.

If the total flow rate Qt is greater than the flow rate threshold ("Y"), the method 7000 proceeds to step 7020, which band-pass filters both the total flow rate Qt and the device pressure Pd to a frequency range that spans the limits of the human breathing rate. Step 7020 is intended to remove components of short-term variation in pressure and flow rate, i.e. oscillations at frequencies greater than the typical breathing rate. Such components are "noise" in the sense that they are of no interest in determining whether high flow therapy is being used by the patient 1000. In one implementation, the upper cutoff frequency of the band-pass filter is 0.5 Hz, which is an approximate upper limit of the human breathing rate at rest. Step 7020 is also intended to remove any components of long-term variation, i.e. oscillations at frequencies that are less than the typical breathing rate. In one implementation, the lower cutoff frequency of the band-pass filter is 0.1 Hz, which is an approximate lower limit of the human breathing rate at rest. The band-pass filtering of step 7020 is configured to leave the mean or steady-state values of the band-pass filtered total flow rate Qt' and device pressure Pd' unchanged from those of the total flow rate Qt and device pressure Pd respectively.

As an alternative to using fixed upper and lower cutoff frequencies, the band-pass filtering step 7020 may first estimate the breathing rate of the patient. This may be done, for example, by finding the location of the highest peak in the Fourier transform (e.g., determined with a fast Fourier transform algorithm), of either the total flow rate Qt, the device pressure Pd, or the ratio of the total flow rate Qt to the device pressure Pd. The ratio is useful because it will have a significant component at the breathing rate regardless of the implementation of the servo-control. The highest peak location is an estimate of the breathing rate of the patient. The upper and lower cutoff frequencies for the band-pass filtering step 7020 may then be derived from the breathing rate estimate. For example, the lower cutoff frequency may be one half the breathing rate estimate, while the upper cutoff frequency may be twice the breathing rate estimate.

A further alternative to using fixed upper and lower cutoff frequencies at step 7020 is to use the patient height to determine the likely upper and lower cutoff frequencies, since the patient height is related to the person's breathing rate at rest by a well-understood physiological relationship. The patient height may be entered as a setting of the RT device 4000 via the input device 4220.

After step 7020, the only components of variation remaining in the band-pass filtered total flow rate Qt' and device pressure Pd' are those at frequencies within the breathing rate frequency band defined by the cutoff frequencies of the band-pass filter applied at step 7020, equal to [0.1 Hz, 0.5 Hz] in one implementation described above. These components of variation within the breathing rate frequency band are superimposed on the (positive) steady-state (mean) values of total flow rate Qt and device pressure Pd.

The next step 7030 calculates a resistance to flow in the air circuit 4170 by dividing the band-pass filtered device pressure Pd' by the band-pass filtered total flow rate Qt'. Because the resistance to flow is calculated from two band-pass filtered signals, the resistance to flow may also be regarded as a band-pass filtered signal, even though it was not directly obtained from band-pass filtering.

Step 7035 then determines whether the resistance to flow is within a predetermined range that is characteristic of a patient 1000 using high flow therapy. In one implementation, the predetermined range is from 0.4 cmH$_2$O per litre/minute to 0.9 cmH$_2$O per litre/minute. If step 7035 determines that the resistance to flow is not within the predetermined range ("N"), the method 7000 proceeds to the step 7070 which returns a value of "false". Resistance to flow is substantially independent of the implementation of the servo-control being applied to the device pressure Pd by the RT device 4000. As mentioned above, in one implementation of the servo-control, all the variation in the breathing frequency band would be in the device pressure Pd. In another implementation of the servo-control, all the variation in the breathing frequency band would be in the total flow rate Qt. In either implementation, and for all intermediate implementations, the ratio of the device pressure Pd to the total flow rate Qt (the resistance to flow) should lie within the predetermined range as long as the patient 1000 is using the high flow therapy. However, this is not a sufficient condition for determining that high flow therapy is being used, so the method 7000 continues to step 7040 if step 7035 determines that the resistance to flow is not within the predetermined range ("Y").

Steps 7040 and 7045 aim to determine whether a property of the delivered flow of air contains a significant oscillation within the human breathing rate frequency band defined by the cutoff frequencies of step 7020. Step 7040 therefore calculates a magnitude of variation of one of the band-pass filtered signals over a sliding window of predetermined duration. In one implementation, step 7040 calculates the standard deviation of the band-pass filtered signal over a sliding window of duration one minute. The standard deviation may be used because it is insensitive to the average value over the window, thus emphasising any oscillations within the window. Other implementations of step 7040 include:

- calculating the magnitude of variation using the number of zero crossings of the mean-subtracted band-pass filtered signal over the sliding window;
- computing the power of the Fourier transform spectrum of the (unfiltered) signal in the breathing rate frequency band computed over the sliding window;
- computing the power of the Fourier transform spectrum of the (unfiltered) signal in harmonics of the breathing rate frequency band computed over the window of predetermined duration, as such harmonics (which indicate for example the presence of snoring) are also indicative of a patient 1000 breathing.

In one implementation of step 7040, suitable for the implementation in which the device pressure Pd remains constant throughout the breathing cycle, the band-pass filtered signal is the band-pass filtered total flow rate Qt'. In another implementation of step 7045, suitable for the implementation in which the total flow rate Qt remains constant throughout the breathing cycle, the band-pass filtered signal is the band-pass filtered device pressure Pd'. In yet another implementation of step 7045, suitable for intermediate implementations of servo-control, the band-pass filtered signal is the resistance to flow calculated at step 7030.

Step 7045 then determines whether the magnitude of variation of the band-pass filtered signal is greater than a magnitude threshold. In one implementation in which the band-pass filtered signal is the band-pass filtered total flow rate Qt', the magnitude threshold is 10 litres/minute. If step 7045 determines that the magnitude of variation of the band-pass filtered signal is not greater than the magnitude threshold ("N"), the method 7000 proceeds to the step 7070 which returns a value of "false".

Otherwise ("Y" at step 7045), the method 7000 proceeds to determine whether the magnitude of variation of the band-pass filtered signal itself (e.g., the band-pass filtered total flow rate Qt') varies significantly as the sliding window over which the magnitude is calculated slides forward. The presence of such variations in the magnitude of variation of the band-pass filtered signal tends to confirm that high flow therapy is being used by the patient 1000, since respiratory demand typically varies slowly over time. Step 7050 therefore calculates a measure of variation of the magnitude of variation of the band-pass filtered signal over a further sliding window of predetermined duration. In one implementation, the further sliding window may be of the same duration as the sliding window over which the magnitude of variation of the band-pass filtered signal was calculated at step 7040. Step 7055 then determines whether the measure of variation of the magnitude of variation of the band-pass filtered signal is greater than a magnitude variation threshold. The magnitude variation threshold may be chosen depending on the duration of the further sliding window. The longer the sliding window, the smaller should be the chosen magnitude variation threshold. In one implementation in which the band-pass filtered signal is the band-pass filtered total flow rate Qt', the further sliding window is of duration one minute, the measure of variation of the magnitude is a variance, and the flow rate magnitude variation threshold is 0.002.

If step 7055 determines that the measure of variation of the magnitude of variation of the band-pass filtered signal is not greater than the magnitude variation threshold ("N"), the method 7000 proceeds to step 7070 which returns a value of "false", indicating that high flow therapy is not in use by the patient 1000. Otherwise ("Y"), the method 7000 proceeds to step 7060 which returns a value of "true", indicating that high flow therapy is being used by the patient 1000.

In alternative implementation of the high flow therapy usage determination algorithm, the steps 7050 and 7055 may be omitted, so that a "Y" answer from step 7045 is immediately followed by step 7060. Steps 7050 and 7055 may therefore be said to be optional.

In alternative implementations of the high flow therapy usage determination algorithm, the steps 7040 and 7045 (and optionally 7050 and 7055) may be carried out on the device pressure Pd or the resistance to flow calculated at step 7030, rather than the total flow rate Qt. In such implementations, different thresholds are applied at steps 7045 (and 7055, if present).

8.4.3.2 High Flow Therapy Monitoring

In one form of the present technology, a high flow therapy monitoring algorithm receives as inputs a signal representative of the pressure Pd at the RT device outlet, and a signal representative of the total flow rate Qt of air being delivered by the RT device 4000. The high flow therapy monitoring algorithm generates as an output a times series of indications of the status of the high flow therapy at successive time instants. The status indication at any time instant can take on one of several values, each indicating a different status of the high flow therapy, for example: "in use", "not in use", "device inactive", "air circuit occluded", and "air circuit disconnected". Such status indication(s) may be stored in a memory 4260 or output for display on a user interface or display of, or in communication with, a controller 4230 of an RT device 4000 that determines the indicator.

As described above in relation to the high flow therapy usage determination algorithm, the high flow therapy monitoring algorithm may be carried out by the central controller 4230 of the RT device 4000, a processor of the remote external computing device 4286, or some combination of the two, in "real time", or as a post-process. Also as described above in relation to the high flow therapy usage determination algorithm, the high flow therapy monitoring algorithm may accumulate the status indications into a record of high flow therapy status over time. The RT device 4000 may take different actions based on such a record of status. For example, in some cases, the status indication or the accumulated record of status indications may be evaluated in the controller to serve as a trigger to change an operation of the controller 4230 of the RT device 4000. By way of example, the controller 4230 may discontinue treatment (e.g., reducing flow generation or stopping flow generation such as by modifying a control operation of the blower motor 4144) for example, when a sufficient number (e.g., in series) of status indications indicate non-use, occluded and/or disconnected. Optionally, the controller 4230 may increase treatment (e.g., increasing flow generation such as by modifying a control operation of the blower motor), for example, when a sufficient number (e.g., in series) of status indications indicate occluded.

FIG. 7B is a flow chart illustrating a method 7100 that may be used to implement the high flow therapy monitoring algorithm in accordance with one form of the present technology. The method 7100 is described below in terms of the device pressure Pd. However, the method 7100 may work effectively using the patient interface pressure Pm, provided appropriate thresholds are set.

The method 7100 is similar to the method 7000 in that steps in the method 7100 with counterpart numbered steps in the method 7000 (e.g. 7130 and 7030) are generally the same as their counterpart numbered steps in the method 7000, except as described below.

The first step 7110 determines whether the device pressure Pd is below a threshold, which can occur if the pressure generator 4140 is not operational or malfunctioning. If so ("Y"), the method 7100 proceeds to step 7115, which concludes the method 7100 and returns a status indication value of "device inactive". Otherwise ("N"), the method 7100 proceeds to steps 7120 and 7130, which are the same as steps 7020 and 7030 as described above.

Step 7133, which follows step 7130, checks whether the resistance to flow is too small, i.e. is lower than the lower end of the range used in step 7035, equal in one implementation to 0.4 cmH$_2$O per litre/minute. If so ("Y"), the method 7100 proceeds to step 7137, which concludes the method 7100 and returns a status indication value of "disconnected" for the indicator. This value indicates that the unsealed patient interface 3800 has been disconnected from the airway of the patient 1000, making the leak resistance 6140 in the circuit model 6100 small.

Otherwise ("N" at step 7133), the method 7100 proceeds to step 7138, which checks whether the resistance to flow is too large, i.e. is higher than the upper end of the range used in step 7035, equal in one implementation to 0.9 cmH$_2$O per litre/minute. If so ("Y"), the method 7100 proceeds to step 7139, which concludes the method 7100 and returns a status indication value of "occluded" for the indicator. This value indicates that the air circuit 4170 may be occluded. If not ("N"), the method 7100 proceeds to step 7140 which is the same as step 7040 described above.

In a variant of the method 7100, the test 7138 is followed by a second test (not shown) of the value of the resistance to flow. If that value is greater than a threshold that is "high", but lower than the threshold used at step 7138, a further step may return a status indication value of "cannula too large", indicating that the cannula prongs are close to sealing with the inside of the nose of the patient 1000.

Step 7170, which is reached if the test at step 7145 or the test at step 7155 is failed (which may for example occur if the patient 1000 experiences an extended apnea or has blocked nasal passages), returns a value of "not in use" for the status indication, indicating that the patient 1000 is not using high flow therapy. Step 7160, which is reached if the test at step 7155 is passed, returns a value of "in use" for the status indication, indicating that the patient 1000 is using high flow therapy.

In a variant of the method 7100 for monitoring high flow therapy, the "return" steps 7115, 7137, and 7139, which return "device inactive", "disconnected", and "occluded" respectively, may be replaced by a test for their respective status indications. For example, step 7137, rather than returning a status indication of "disconnected" may initiate a separate test for disconnection of the unsealed patient interface 3800 from the patient 1000.

8.4.3.3 Circuit Model Calibration

The circuit model 6100 may be generalised such that the air circuit, the interface, and the leak path are no longer modelled by linear resistances 6130, 6150, and leak resistance 6140 respectively, but by respective non-linear impedances whose pressure drop depends non-linearly on the flow rate of air passing through them. To characterise each of these impedances, multi-stage calibration may be undertaken. In each stage, at least two different values of steady-state device pressure Pd are applied and corresponding measurements of total flow rate Qt are taken. The applied values and measurements are used to fit a polynomial relating the pressure drop across the impedance to the flow rate therethrough. The following sequence of calibration stages may be employed, each listing a configuration of the air circuit and the corresponding impedance that may be characterised thereby. The impedance characterised by each stage enables the next stage of calibration/characterisation.

interface disconnected from air circuit: air circuit impedance corresponding to resistance element 6130.

interface connected to air circuit but disconnected from patient: interface impedance corresponding to resistance element 6150.

interface connected to air circuit and to patient, patient "self-occluding": leak impedance corresponding to resistance element 6140.

8.4.3.4 Patient Parameter Estimation

It may be of diagnostic interest to estimate parameters of the patient 1000 such as the airway resistance 6125, the lung compliance 6135, an airway "inertance" modelled in the circuit model 6100 by an inductor (not shown) in series with those elements, and parameters derivable from these values such as the lung resonance frequency (equal to the reciprocal of the square root of the product of the inertance and the compliance, divided by $2\pi$) and the attenuation (equal to the resistance divided by twice the inertance). To estimate such parameters, the source 6110 may have a more "active" component superimposed on its servo-controlled value, whether the servo-controlled value is constant or varying at the breathing rate, as described above. The active component may, for example, comprise an impulse, a ramp, an oscillation at a certain frequency, or wideband noise. The resulting response of the total flow rate Qt may be analysed along with the active component of the device pressure Pd to generate an estimate of one or more of the above-mentioned patient parameters. This process is greatly aided if the non-patient elements of the circuit model 6100 (6130, 6150, and 6140) have previously been characterised by calibration, as previously described.

8.4.3.5 Two-Nostril Model

FIG. 6C is a circuit diagram of an electrical circuit model 6200 that forms a still more sophisticated model of an RT device delivering high flow therapy to a breathing patient 1000 via an unsealed patient interface 3800. The electrical circuit model 6200 contains elements 6210, 6220, 6225, 6230, and 6235 that are the same as their respective counterparts 6110, 6120, 6120, 6125, 6130, and 6135 in the electrical circuit model 6100. The circuit model 6200, however, divides the interface resistance 6150 into two separate resistances 6250a and 6250b modelling the left and right nasal prongs respectively of the unsealed patient interface 3800. The leak resistance 6140 is also separated into left and right nostril leak resistances 6240a and 6240b respectively. The variable nature of resistances 6260a and 6260b model the resistances of the left and right nasal passages respectively. The total flow rate Qt divides into the flow rate Qa through the left prong and the flow rate Qb through the right prong.

If the nasal passage resistances 6260a and 6260b are very small, then the model 6200 simplifies to the model 6100 with the interface resistance 6150 equal to the resistances 6250a and 6250b in parallel, and the leak resistance 6140 equal to the left and right nostril leak resistances 6240a and 6240b in parallel. However, if either of the nasal passage resistances 6260a and 6260b is non-negligible, which occurs for example due to nasal cycling, this will not be the case. The above-described usage determination and monitoring methods are still applicable to the two-nostril model 6200 to determine usage indications and status indications at a given time, though potentially implemented with different threshold values from those previously identified. However, to characterise the individual nostril and leak resistances at any given time would require a more elaborate version of the multi-stage calibration process described above:

- interface disconnected from air circuit: air circuit impedance corresponding with resistance element 6230.
- interface connected to air circuit but disconnected from patient, right prong blocked: left prong impedance corresponding with resistance element 6250a.
- interface connected to air circuit but disconnected from patient, left prong blocked: right prong impedance corresponding with resistance element 6250b.
- interface connected to air circuit and to patient, patient "self-occluding" right nostril: left nostril leak impedance corresponding with resistance element 6240a.
- interface connected to air circuit and to patient, patient "self-occluding" left nostril: right nostril leak impedance corresponding with resistance element 6240b.

Addition of an "active" component to the source 6110 with each nostril self-occluded in turn, followed by analysis of the active components and the resulting total flow rates Qt, may then allow the left and right nasal passage impedances respectively corresponding with resistance element 6260a and resistance element 6260b to be estimated along with the other patient parameters at any given time.

8.5 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240. The humidifier reservoir 5110 may comprise a conductive portion 5120 configured to allow efficient transfer of heat from the heating element 5240 to the volume of liquid in the reservoir 5110. The humidifier reservoir 5110 may comprise a water level indicator 5150.

In one form, the humidifier 5000 may comprise a humidifier reservoir dock 5130 configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

8.6 Glossary

For the purposes of the present technology disclosure, in certain forms of the present technology, one or more of the following definitions may apply. In other forms of the present technology, alternative definitions may apply.

8.6.1 General

Air: In certain forms of the present technology, air may be taken to mean atmospheric air, and in other forms of the present technology air may be taken to mean some other combination of breathable gases, e.g. atmospheric air enriched with oxygen.

Respiratory Pressure Therapy: The delivery of air to an entrance to the airways at a treatment pressure that is continuously positive with respect to atmosphere.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is continuously adjustable, e.g. from breath to breath, between minimum and maximum limits, depending on the presence or absence of indications of SDB events.

8.6.2 Aspects of the Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
 (i) a 30% reduction in patient breathing for at least 10 seconds plus an associated 4% desaturation; or
 (ii) a reduction in patient breathing (but less than 50%) for at least 10 seconds, with an associated desaturation of at least 3% or an arousal.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These synonymous terms may be understood to refer to the RT device's estimate of respiratory airflow rate, as opposed to "true respiratory flow" or "true respiratory airflow", which is the actual respiratory flow rate experienced by the patient, usually expressed in litres/minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

8.6.3 RT Device Parameters

Flow rate: The instantaneous volume (or mass) of air delivered per unit time. ('Flow rate' is sometimes shortened to simply 'flow'). While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Total flow rate, Qt, is the flow rate of air being delivered by the RT device.

Pressure: Force per unit area. Pressure may be measured in a range of units, including $cmH_2O$, $g\text{-}f/cm^2$, hectopascal. 1 $cmH_2O$ is equal to 1 $g\text{-}f/cm^2$ and is approximately 0.98 hectopascal. In this specification, unless otherwise stated, pressure is given in units of $cmH_2O$. The pressure in the patient interface (the patient interface pressure) is given the symbol Pm, while the pressure at the outlet of the RT device (the device pressure) is given the symbol Pd.

8.7 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

8.8 REFERENCE SIGNS LIST patient 1000
bed partner 1100
patient interface 3000
seal-forming structure 3100
plenum chamber 3200
structure 3300
vent 3400
connection port 3600
forehead support 3700
unsealed patient interface 3800
nasal prongs 3810
nasal prongs 3810
lumen 3820
lumen 3820
RT device 4000
external housing 4010
upper portion 4012
portion 4014
panel 4015
chassis 4016
handle 4018
pneumatic block 4020
pneumatic components 4100
air filter 4110
inlet air filter 4112
outlet air filter 4114
inlet muffler 4122
outlet muffler 4124
pressure generator 4140
blower 4142
motor 4144
air circuit 4170
supplemental oxygen 4180
electrical components 4200
Printed Circuit Board Assembly 4202
electrical power supply 4210
input device 4220
central controller 4230
clock 4232
therapy device controller 4240
protection circuits 4250
memory 4260
transducers 4270
pressure sensors 4272
flow rate transducer 4274
motor speed transducer 4276
data communication interface 4280
remote external communication network 4282
local external communication network 4284
remote external computing device 4286
local external device 4288
output device 4290
display driver 4292
display 4294
algorithms 4300
therapy control module 4330
humidifier 5000
humidifier inlet 5002
humidifier outlet 5004
humidifier base 5006
humidifier reservoir 5110
conductive portion 5120
humidifier reservoir dock 5130
locking lever 5135
water level indicator 5150
heating element 5240
humidifier controller 5250
electrical circuit model 6000
voltage source 6010
AC voltage source 6020
airway resistance 6025
air circuit resistance 6030
lung compliance 6035
interface resistance 6050
electrical circuit 6100
voltage source 6110
AC voltage source 6120
airway resistance 6125
air circuit resistance 6130
lung compliance 6135
leak resistance 6140
interface resistance 6150 electrical circuit 6200
voltage source 6210
AC voltage source 6220
airway resistance 6225
air circuit resistance 6230
lung compliance 6235
left nostril leak impedance 6240*a*
right nostril leak impedance 6240*b*
left prong impedance 6250*a*
right prong impedance 6250*b*
left nasal passage impedance 6260*a*
right nasal passage impedance 6260*b*
method 7000
step 7010
step 7020
step 7030
step 7035
step 7040
step 7045
step 7050
step 7055
step 7060
step 7070
method 7100
step 7110
step 7115
step 7120
step 7130
step 7133
step 7137
step 7138
step 7139
step 7140
step 7145
step 7155
step 7160
step 7170

The invention claimed is:

1. A method of determining whether high flow therapy is being used by a patient, the method comprising:
calculating, in a controller associated with a respiratory therapy device, a resistance to a flow of air delivered during a high flow therapy operation mode by the respiratory therapy device along an air circuit to an unsealed patient interface,
determining, in the controller, whether a property of the flow of air being delivered during the high flow therapy operation mode by the respiratory therapy device along the air circuit to the unsealed patient interface contains a significant oscillation within a breathing rate frequency band, wherein the property of the flow of air is the resistance to flow and the significant oscillation results from a patient using high flow therapy when the unsealed patient interface is coupled at the patient's airway entrance, wherein the determining comprises:
  (i) calculating, in the controller, a magnitude of variation of the resistance to flow within the breathing rate frequency band and over a window of predetermined duration, and
  (ii) comparing, in the controller, the magnitude of variation to a magnitude threshold to determine whether the magnitude of variation is greater than the magnitude threshold,
determining, in the controller, whether the resistance to flow is within a predetermined range by comparing the resistance to flow to an upper end of the predetermined range and comparing the resistance to flow to a lower end of the predetermined range, wherein the predetermined range is selected such that resistance values contained within the predetermined range characterize the unsealed patient interface during patient use of high flow therapy when the unsealed patient interface is coupled at the patient's airway entrance so as to omit resistance values that characterize resistance when the unsealed patient interface is receiving flow in the high flow therapy operation but is not coupled at the patient's airway entrance,
generating, in the controller, a plurality of output indications of whether high flow therapy is being used by the patient over time such that each output indication of the plurality of output indications indicates that the patient interface is coupled to the patient's airway entrance and the high flow therapy is being received by the patient, wherein the generating comprises generating an output indication, of the plurality of output indications, based on a determination that (a) the magnitude of variation of the resistance to flow is greater than the magnitude threshold, (b) the resistance to flow is less than the upper end of the predetermined range, and (c) the resistance to flow is greater than the lower end of the predetermined range,
determining, in the controller, an amount of usage time of high flow therapy based on the plurality of output indications, and
the controller controlling a change in operation of the respiratory therapy device based on at least one of the plurality of output indications of whether high flow therapy is being used by the patient.

2. A method according to claim 1, wherein the magnitude of variation is a standard deviation over the window.

3. A method according to claim 1, wherein the calculating the magnitude of variation comprises computing a power of a Fourier transform spectrum of the resistance to flow over the window within the breathing rate frequency band.

4. A method according to claim 1, further comprising determining whether the magnitude of variation varies significantly as the window slides forward.

5. A method according to claim 4, wherein the generating generates the plurality of output indications based on a determination that the magnitude of variation varies significantly as the window slides forward.

6. A method according to claim 4, wherein the determining whether the magnitude of variation varies significantly as the window slides forward comprises:
calculating a measure of variation of the magnitude of variation over a further window of predetermined duration, and
determining whether the measure of variation is greater than a magnitude variation threshold.

7. A method according to claim 6, wherein the measure of variation is a variance.

8. A method according to claim 1, wherein the resistance to flow is calculated from a total flow rate of the flow of air and a pressure of the flow of air.

9. A method according to claim 8, wherein the calculating the resistance to flow comprises:
applying, to the total flow rate and the pressure, a band-pass filter with cutoff frequencies being approximate upper and lower limits of human breathing rate at rest, to produce a band-pass filtered device pressure and a band-pass filtered total flow rate, and
dividing the band-pass filtered device pressure by the band-pass filtered total flow rate.

10. A method according to claim 9, wherein the pressure is a pressure at an outlet of the respiratory therapy device.

11. A method according to claim 1, further comprising generating, in the controller, at least one output indication to indicate that high flow therapy is not being used by the patient upon a determination that the resistance to flow is not within the predetermined range.

12. A method according to claim 1, further comprising generating, in the controller, at least one output indication to indicate that the unsealed patient interface has been disconnected from the patient's airway entrance upon a determination that the resistance to flow is lower than a lower end of the predetermined range.

13. A method according to claim 1, further comprising generating, in the controller, at least one output indication to indicate that the air circuit has been occluded upon a determination that the resistance to flow is higher than an upper end of the predetermined range.

14. A method according to claim 1, further comprising generating, in the controller, dependent on the determining whether the resistance to flow is within the predetermined range, an output indication to indicate that the patient interface is too large upon a determination that the resistance to flow is higher than an upper end of the predetermined range.

15. A method according to claim 1, further comprising accumulating the generated plurality of output indications into a record of usage of the high flow therapy by the patient over time.

16. A method according to claim 15, further comprising generating a compliance report based on the record of usage of the high flow therapy.

17. A method according to claim 15, further comprising adjusting a parameter of the high flow therapy based on the record of usage of the high flow therapy.

18. A method according to claim 17, wherein the parameter is a therapeutic flow rate.

19. A method according to claim 15, further comprising generating an alarm based on the record of usage of the high flow therapy.

20. A method according to claim 1, further comprising:
comparing, in the controller, a total flow rate of the flow of air with a flow rate threshold, and
generating, in the controller, at least one output indication to indicate that high flow therapy is not being used by the patient upon a determination that the total flow rate is less than the flow rate threshold based on the comparing.

21. A method according to claim 1, further comprising:
comparing, in the controller, a pressure of the flow of air with a pressure threshold, and
generating, in the controller, at least one output indication to indicate that the respiratory therapy device is inactive upon a determination that the pressure is less than the pressure threshold based on the comparing.

22. A method according to claim 1, further comprising estimating a breathing rate from a signal representing the property.

23. A method according to claim 22, wherein the breathing rate frequency band comprises a frequency band with upper and lower cutoff frequencies derived from the estimated breathing rate.

24. A method according to claim 23, wherein the lower cutoff frequency is one half the estimated breathing rate and upper cutoff frequency is twice the estimated breathing rate.

25. The method according to claim 1 wherein the change in operation of the respiratory therapy device changes a property of the flow of air being delivered by the respiratory therapy device.

26. A method according to claim 1, further comprising generating, in the controller, an output indication indicating that high flow therapy is not being used by the patient based on a determination that (a) the property of the flow of air does not contain a significant oscillation, or (b) the resistance to flow is not within the predetermined range.

27. A method according to claim 1, wherein the plurality of output indications comprises a time series of Boolean usage indications of whether high flow therapy is being used by the patient at successive time instants.

28. An apparatus for delivering high flow therapy to a patient, the apparatus comprising:
a servo-controlled blower configured to generate a flow of air along an air circuit to an unsealed patient interface during a high flow therapy operation mode;
a central controller configured to control the servo-controlled blower;
one or more transducers configured to generate one or more signals representing respective properties of the flow of air being generated; and
a processor configured to:
receive the one or more signals;
control a calculation of a resistance to the flow of air based on the one or more signals;
control a determination of whether a property of the flow of air contains a significant oscillation within a breathing rate frequency band, wherein the property of the flow of air is the resistance to flow and the significant oscillation results from a patient using high flow therapy when the unsealed patient interface is coupled at the patient's airway entrance, wherein the determination comprises:
(i) calculating a magnitude of variation of the resistance to flow within the breathing rate frequency band and over a window of predetermined duration, and
(ii) comparing the magnitude of variation to a magnitude threshold to determine whether the magnitude of variation is greater than the magnitude threshold;
control a determination of whether the resistance to flow is within a predetermined range by comparing the resistance to flow to an upper end of the predetermined range and comparing the resistance to flow to a lower end of the predetermined range, wherein the predetermined range is selected such that resistance values contained within the predetermined range characterize the unsealed patient interface during patient use of high flow therapy when the unsealed patient interface is coupled at the patient's airway entrance, so as to omit resistance values that characterize resistance when the unsealed patient interface is receiving flow in the high flow therapy operation but is not coupled at the patient's airway entrance;
generate a plurality of indications of whether high flow therapy is being used by the patient over time such that each output indication of the plurality of output indications indicates that the patient interface is coupled to the patient's airway entrance and the high flow therapy is being received by the patient, wherein the generating comprises generating an output indication, of the plurality of output indications, based on a determination that (a) the magnitude of variation of the resistance to flow is greater than the magnitude threshold, (b) the resistance to flow is less than the upper end of the predetermined range, and (c) the resistance to flow is greater than the lower end of the predetermined range;

determine an amount of usage time of high flow therapy by accumulating the plurality of indications, and control a change in operation of the respiratory therapy device based on at least one of the plurality of output indications of whether high flow therapy is being used by the patient.

29. Apparatus according to claim 28, wherein the processor is the central controller.

30. Apparatus according to claim 28, wherein the processor is located in a remote external computing device configured to communicate with the central controller.

31. An apparatus for delivering high flow therapy to a patient, the apparatus comprising:

flow means for generating a flow of air along an air circuit to an unsealed patient interface during a high flow therapy operation mode;

means for controlling the flow means;

means for generating one or more signals representing respective properties of the flow of air being generated;

means for receiving the one or more signals;

means for calculating a resistance to the flow of air based on the one or more signals;

means for determining whether a property of the flow of air contains a significant oscillation within a breathing rate frequency band, wherein the property of the flow of air is a resistance to flow and the significant oscillation results from a patient using high flow therapy when the unsealed patient interface is coupled at the patient's airway entrance, wherein the means for determining comprises:

(i) means for calculating a magnitude of variation of the resistance to flow within the breathing rate frequency band and over a window of predetermined duration, and (ii) means for comparing the magnitude of variation to a magnitude threshold to determine whether the magnitude of variation is greater than the magnitude threshold;

means for determining whether the resistance to flow is within a predetermined range by comparing the resistance to flow to an upper end of the predetermined range and comparing the resistance to flow to a lower end of the predetermined range, wherein the predetermined range is selected such that resistance values contained within the predetermined range characterize the unsealed patient interface during patient use of high flow therapy when the unsealed patient interface is coupled at the patient's airway entrance, so as to omit resistance values that characterize resistance when the unsealed patient interface is receiving flow in the high flow therapy operation but is not coupled at the patient's airway entrance;

means for generating a plurality of indications of whether high flow therapy is being used by the patient over time such that each output indication of the plurality of output indications indicates that the patient interface is coupled to the patient airway entrance and the high flow therapy is being received by the patient, wherein the means for generating comprises generating an output indication, of the plurality of output indications, based on a determination that (a) the magnitude of variation of the resistance to flow is greater than the magnitude threshold, (b) the resistance to flow is less than the upper end of the predetermined range, and (c) the resistance to flow is greater than the lower end of the predetermined range;

means for determining an amount of usage time of high flow therapy based on the plurality of indications, and wherein the means for controlling controls a change in operation of the respiratory therapy device based on at least one of the plurality of output indications of whether high flow therapy is being used by the patient.

32. A high flow therapy system comprising:

an unsealed patient interface;

an air circuit configured to be connected to the unsealed patient interface;

a servo-controlled blower configured to generate a flow of air along an air circuit during a high flow therapy operation mode;

a central controller configured to control the servo-controlled blower;

one or more transducers configured to generate one or more signals representing respective properties of the flow of air being generated; and a processor configured to:

receive the one or more signals;

control a calculation of a resistance to flow based on the one or more signals;

control a determination of whether a property of the flow of air contains a significant oscillation within a breathing rate frequency band, wherein the property of the flow of air is the resistance to flow and the significant oscillation results from a patient using high flow therapy when the unsealed patient interface is coupled at the patient's airway entrance, wherein the determination comprises:

(i) calculating a magnitude of variation of the resistance to flow within the breathing rate frequency band and over a window of predetermined duration; and (ii) comparing the magnitude of variation to a magnitude threshold to determine whether the magnitude of variation is greater than the magnitude threshold;

control a determination of whether the resistance to flow is within a predetermined range by comparing the resistance to flow to an upper end of the predetermined range and comparing the resistance to flow to a lower end of the predetermined range, wherein the predetermined range is selected such that resistance values contained within the predetermined range characterize the unsealed patient interface during patient use of high flow therapy when the unsealed patient interface is coupled at the patient's airway entrance, so as to omit resistance values that characterize resistance when the unsealed patient interface is receiving flow in the high flow therapy operation but is not coupled at the patient's airway entrance;

generate a plurality of indications of whether high flow therapy is being used by the patient over time such that each output indication of the plurality of output indications indicates that the patient interface is coupled to the patient airway entrance and the high flow therapy is being received by the patient, wherein the generating comprises generating an output indication, of the plurality of output indications, based on a determination that (a) the magnitude of variation of the resistance to flow is greater than the magnitude threshold, (b) the resistance to flow is less than the upper end of the predetermined range, and (c) the resistance to flow is greater than a lower end of the predetermined range;

determine an amount of usage time of high flow therapy based on the plurality of indications, and control a change in operation of the respiratory therapy device based on at least one of the plurality of output indications of whether high flow therapy is being used by the patient.

\* \* \* \* \*